(12) United States Patent
Gulati

(10) Patent No.: US 7,567,876 B2
(45) Date of Patent: Jul. 28, 2009

(54) QUANTUM RESONANCE INTERFEROMETRY FOR DETECTING SIGNALS

(75) Inventor: Sandeep Gulati, La Canada, CA (US)

(73) Assignee: ViaLogy LLC, Altadena, CA (US)

( * ) Notice: Subject to any disclaimer, the term of this patent is extended or adjusted under 35 U.S.C. 154(b) by 0 days.

(21) Appl. No.: 11/835,378

(22) Filed: Aug. 7, 2007

(65) Prior Publication Data

US 2008/0033672 A1    Feb. 7, 2008

Related U.S. Application Data

(60) Provisional application No. 60/836,211, filed on Aug. 7, 2006.

(51) Int. Cl.
*G06F 17/40* (2006.01)
*G06F 17/00* (2006.01)

(52) U.S. Cl. ................ 702/69; 702/189; 702/193; 356/450

(58) Field of Classification Search ............ 702/69, 702/193, 189
See application file for complete search history.

(56) References Cited

U.S. PATENT DOCUMENTS

| | | | |
|---|---|---|---|
| 6,136,541 A * | 10/2000 | Gulati | ............ 435/6 |
| 6,142,681 A | 11/2000 | Gulati | |
| 6,671,625 B1 * | 12/2003 | Gulati | ............ 702/20 |
| 7,006,680 B2 | 2/2006 | Gulati | |
| 2004/0064261 A1 * | 4/2004 | Gulati | ............ 702/19 |
| 2004/0111219 A1 * | 6/2004 | Gulati | ............ 702/19 |
| 2006/0053005 A1 | 3/2006 | Gulati | |
| 2007/0250280 A1 * | 10/2007 | Beausoleil et al. | ............ 702/79 |

OTHER PUBLICATIONS

Renka et al., "Scattered Data Fitting Using a constrained Delaunay Traingulation", IMACS '91, 13th World Congress on Computation and Applied Mathematics, Jul. 22-26, 1991, vol. 1, pp. 122-123.

* cited by examiner

*Primary Examiner*—Hal D Wachsman
(74) *Attorney, Agent, or Firm*—Fish & Richardson P.C.

(57) ABSTRACT

Systems and apparatus related to quantum resonance interferometry for detecting signals are described. First and second signals are received and coupled with a first function and a second function, respectively, generated from a first quantum mechanical system and a second quantum mechanical system, respectively. By doing so, a first tunneling rate and a second tunneling rate are generated. The first tunneling rate is coupled with a third function generated from a third quantum mechanical system. The second tunneling rate is coupled with the third function to obtain a third tunneling rate. Upon determining that the third tunneling rate is greater than a threshold, it is identified that the second signal corresponds to the first signal.

28 Claims, 11 Drawing Sheets

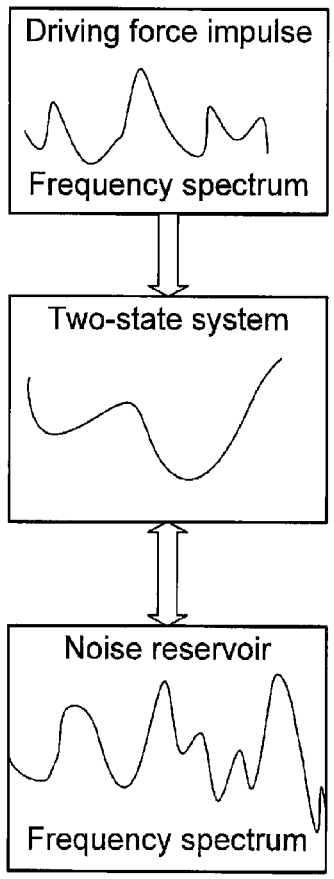
FIG. 8A
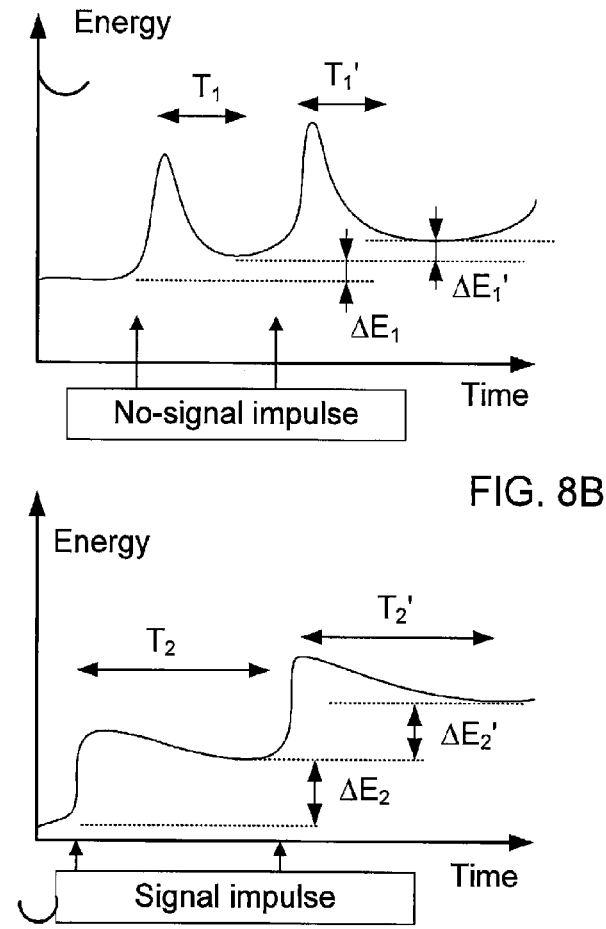
FIG. 8B
FIG. 8C
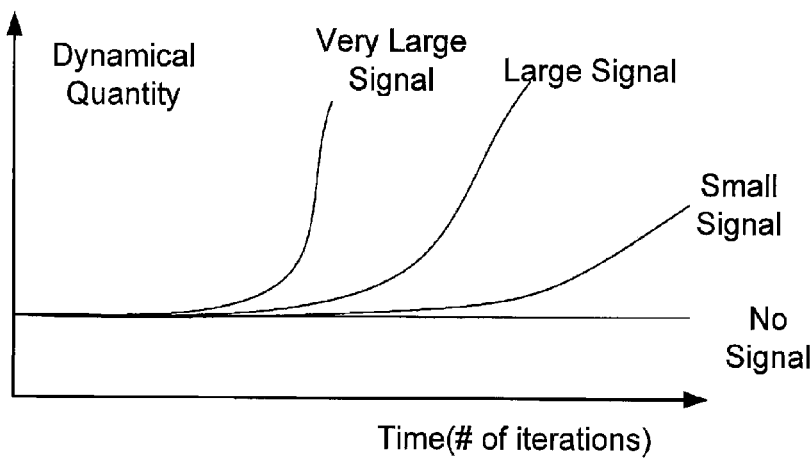
FIG. 8D

QUANTUM RESONANCE INTERFEROMETRY FOR DETECTING SIGNALS

CROSS REFERENCE TO RELATED APPLICATIONS

This application claims the benefit of the priority of U.S. Provisional Application Ser. No. 60/836,211 filed on Aug. 7, 2006, and entitled "QRI PREAMPLIFIER FOR ENHANCING GPS RECEIVER PERFORMANCE."

INCORPORATION BY REFERENCE OF A COMPUTER PROGRAM LISTING

An electronic version of the computer program listing is filed herewith, the contents of which are incorporated by reference in their entirety. The computer-readable file, created on Aug. 7, 2007, is entitled 18329025001CompProgList.txt.

TECHNICAL FIELD

This disclosure relates to signal detection and noise reduction using techniques, e.g., quantum resonance interferometry.

BACKGROUND

Experimentally acquired data typically includes noise in addition to signals representing information and/or events of interest. The noise represents undesired variations that are not related to the desired data. For example, the acquired data can include stochastic variations generated by interactions with the environment surrounding a measured system or a detector acquiring the data. Noise can be generated within the measured system by events that are unrelated to the information of interest. Noise may also be generated when the acquired data is transmitted or processed, for example, when it is digitized. Noise can be a significant problem with devices employing an array of sensors in which there are numerous sources of signals.

Interferometry can measure very small differences in lengths, distances and changes in dimension density and other properties by the interference of two waves of light for optical imaging and communication applications. Quantum Resonance Interferometry (QRI) delivers signal-to-noise enhancement by interference between a wave equation representation of both the sensor-specific noise model and unknown wave equation representation of both the sensor-specific noise model and unknown incoming data containing a potential target or event of interest. Within the QRI formalism, signal can represent a specific target signature of interest, and all other target nonspecific background (including sensor) noise and clutter can be noise. QRI hypothesizes signal as a disturbance to noise, and re-formulates target detection/discrimination problems to be developing a compact a noise model for sensor physics.

SUMMARY

In one embodiment, a first signal and a second signal, both buried in noise, are received where the first signal can be a reference signal and the second signal can be a signal obtained from an unknown source. A noise model, representing the first signal, can be generated and interferometrically coupled with an expressor function to detect quantum stochastic resonance (QSR). The QSR determination can identify a first tunneling rate corresponding to the first signal. Similarly, a noise model, representing the second signal, can be generated and interferometrically coupled with an expressor function to detect QSR, and a second tunneling rate corresponding to the second signal can be determined. Subsequently, the first tunneling rate and the second tunneling rate can be interferometrically coupled with an expressor function to enable determining if the second signal corresponds to the first signal. The interferometric coupling of the first and second tunneling rates with an expressor function can produce a third tunneling rate which can indicate that the second signal corresponds to the first signal if the third tunneling rate is greater than a threshold. For example, if the third tunneling rate is greater than the threshold, then the unknown signal can be substantially identical to the reference signal, thereby enabling identifying the source of the second signal.

In one aspect, a computer-implemented method for signal analysis is described. The method includes receiving a first signal, receiving a second signal, coupling the first signal with a first function generated from a first quantum mechanical system to generate a first tunneling rate, coupling the second signal with a second function generated from a second quantum mechanical system to generate a second tunneling rate, coupling the first tunneling rate with a third function generated from a third quantum mechanical system, coupling the second tunneling rate with the third function, obtaining a third tunneling rate, and upon determining that the third tunneling rate is greater than a threshold, identifying that the second signal corresponds to the first signal.

This, and other aspects, can include one or more of the following features. The first signal can be a reference signal and the second signal can be an unknown signal. The second signal can be substantially similar to the first signal if the second signal corresponds to the first signal. Coupling the first signal with a first function can include initializing a first dynamical system corresponding to a first modality of the first signal, generating a first measurement probe based on the initialized first dynamical system, injecting the first measurement probe into the first quantum mechanical system, and determining whether the injection of the first measurement probe into the first quantum mechanical system results in a collapse of the first quantum mechanical system. A collapse of the first quantum mechanical system can indicate resonance between the first measurement probe and the first quantum mechanical system. The first tunneling rate and the second tunneling rate can be pre-conditioned prior to coupling with the third function. Pre-conditioning the first tunneling rate and the second tunneling rate can include converting the first tunneling rate and the second tunneling rate into respective spectral domains.

In another aspect, a computer-implemented method for signal analysis is described. The method includes receiving an unknown signal, coupling the unknown signal with a function generated from a quantum mechanical system to generate a tunneling rate associated with the unknown signal, pre-conditioning the tunneling rate, coupling the pre-conditioned tunneling rate with a reference tunneling rate obtained from a reference signal to generate an output tunneling rate, and upon determining that the output tunneling rate is greater than a threshold, determining that the unknown signal corresponds to the reference signal.

This, and other aspects, can include one or more of the following features. The unknown signal can include one of the reference signal, noise, or a non-specific signal. Coupling the unknown signal with the function can include initializing a dynamical system corresponding to a modality of the unknown signal, generating a measurement probe based on the initialized dynamical system, injecting the measurement probe into the quantum mechanical system, and determining whether the injection of the measurement probe into the quantum mechanical system results in a collapse of the quantum mechanical system. A collapse of the quantum mechanical system can indicate resonance between the measurement probe and the quantum mechanical system. The method can further include pre-conditioning the tunneling rate by applying a Fast Fourier Transform. The reference tunneling rate can be pre-conditioned prior to coupling with the pre-conditioned tunneling rate. The reference signal can be obtained from a known source. Determining that the unknown signal corresponds to the reference signal can include determining that the unknown signal is substantially similar to the reference signal.

In another aspect, a system for signal analysis is described. The system includes a function generator to generate a first function, a second function, and a third function from one or more quantum mechanical systems, a first interferometric coupler to couple a first signal with the first function to generate a first tunneling rate, a second interferometric coupler to couple a second signal with the second function to generate a second tunneling rate, a first pre-conditioner to pre-condition the first tunneling rate, a second pre-conditioner to pre-condition the second tunneling rate, a third interferometric coupler to couple the pre-conditioned first tunneling rate with the third function and to couple the pre-conditioned second tunneling rate with the third function, the third interferometric coupler configured to generate a third tunneling rate, and a comparator to compare the third tunneling rate with a threshold to determine if the third tunneling rate is greater than, or less than or equal to the threshold.

This, and other aspects, can include one or more of the following features. The first signal can be a reference signal and the second signal can be an unknown signal. The second signal can be substantially similar to the first signal if the third tunneling rate is greater than the threshold. The first interferometric coupler can be configured to perform operations including initializing a first dynamical system corresponding to a first modality of the first signal, generating a first measurement probe based on the initialized first dynamical system, injecting the first measurement probe into the first quantum mechanical system, and determining whether the injection of the first measurement probe into the first quantum mechanical system results in a collapse of the first quantum mechanical system. A collapse of the first quantum mechanical system can indicate resonance between the first measurement probe and the first quantum mechanical system.

In another aspect, a computer program product, tangibly embodied in a computer-readable medium is described. The computer program product is configured to cause a machine to perform operations. The operations include receiving an unknown signal, coupling the unknown signal with a function generated from a quantum mechanical system to generate a tunneling rate associated with the unknown signal, pre-conditioning the tunneling rate, coupling the pre-conditioned tunneling rate with a reference tunneling rate obtained from a reference signal to generate an output tunneling rate, and upon determining that the output tunneling rate is greater than a threshold, determining that the unknown signal corresponds to the reference signal.

This, and other aspects, can include one or more of the following features. The unknown signal can include one of the reference signal, noise, or a non-specific signal. Coupling the unknown signal with the function can include initializing a dynamical system corresponding to a modality of the unknown signal, generating a measurement probe based on the initialized dynamical system, generating a measurement probe based on the initialized dynamical system, injecting the measurement probe into the quantum mechanical system, and determining whether the injection of the measurement probe into the quantum mechanical system results in a collapse of the quantum mechanical system. A collapse of the quantum mechanical system can indicate resonance between the measurement probe and the quantum mechanical system. The operations can further include pre-conditioning the tunneling rate by applying a Fast Fourier Transform. The reference tunneling rate can be pre-conditioned prior to coupling with the pre-conditioned tunneling rate. The reference signal can be obtained from a known source. Determining that the unknown signal corresponds to the reference signal can include determining that the unknown signal is substantially similar to the reference signal.

The systems and techniques described here can present one or more of the following advantages. Signals below the noise level can be detected for a large number of different microarray types, including glass based, thin film, electronic, bead or quantum dot arrays. The signal analysis is not limited to particular methods or apparatus that are used to acquire the data. If the reference signal is obtained from a human and the unknown signal is obtained from two sources, e.g., a tree and a human standing next to the tree, the noise reduction technique can detect that the unknown signal includes signal from the human and from the tree. Noise can be analyzed in reference samples to define a non-linear dynamical model for signal analysis. The non-linear dynamical model can be defined "off-line," i.e., before analyzing actual samples. The same non-linear dynamical model can be used for the same pre-characterized platform. With the present techniques, a large number of samples can be analyzed in a short time.

The details of one or more implementations are set forth in the accompanying drawings and the description below. Other features and advantages will be apparent from the description and drawings, and from the claims.

DESCRIPTION OF DRAWINGS

FIG. 8A-8D are illustrations of using a driving force impulse to excite a two-state system.

Like reference symbols in the various drawings indicate like elements.

DETAILED DESCRIPTION

Figure 1:
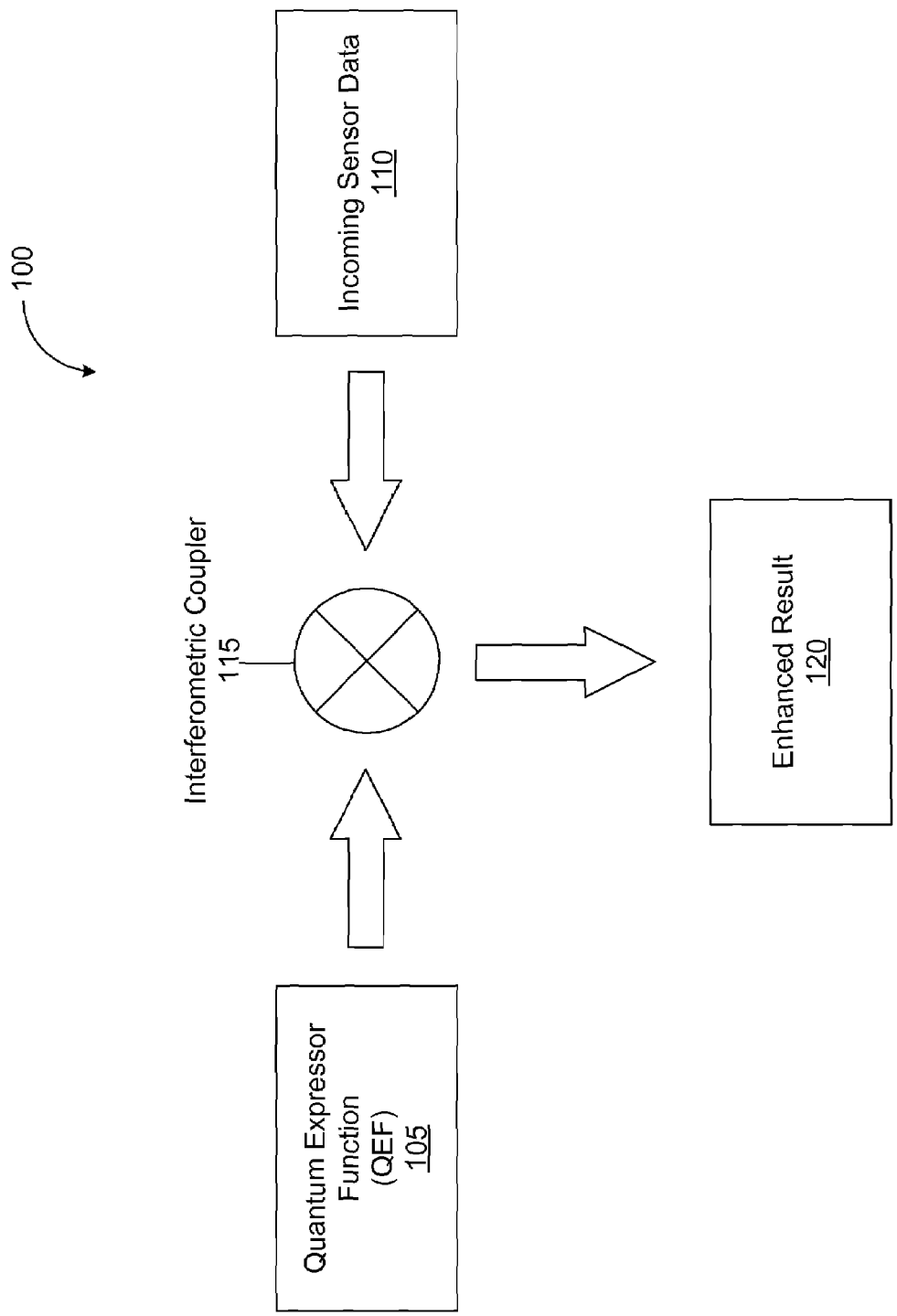
FIG. 1 is an example of a schematic of an interferometric system.

In QRI, a compact set of training samples, including exemplars of targets of interest, representative backgrounds, and operational sensor modalities are used to develop a quantum expresser function (QEF). This can also be referred to as the non-specific target noise model for the sensor. QRI uses a computational engine to implement the interaction between the QEF (or probing noise stimulus) and the incoming uncharacterized signals of interest. As the acquired data includes noise, in addition to signals representing information and events of interest, QRI addresses multiple sources of noise simultaneously. For example, the acquired data can include stochastic variations generated by interactions with the environment surrounding a measurement system or a detector acquiring the data. Clutter or background noise can be generated within the measurement system by the events that are unrelated to the information of interest. For example, noise can be generated when the acquired data is digitized or transmitted. QEF represents the "noise model" for the system for a pre-specified target performance condition, e.g., detectability down to a given limit of detection (LOD). The QEF fidelity is modality specific, e.g., a collection of pixels on a focal plane, a spectral segment of absolute abundance data for a mass spec detector, and the like. The QEF fidelity can correspond to the minimum amount of signal required within incoming data required to conclude signal presence. The incoming unknown data can initially be assumed to be all noise. Interferometric computations between QEF and the incoming data to induce computational resonances can be used to detect signal, as a departure to noise behavior wherein no resonances are observed.

In some implementations of a QRI solution, unknown incoming signals and apriori generated QEF can both be mathematically represented to initialize a wave equation system. QRI leverages the dynamics and properties of a well understood 1-D Spin-Boson quantum mechanical system to develop the wave equation mathematical representation for incoming sensor data and noise model. The two wave equations are destructively interfered to detect the presence of a target buried in noise. An optimal and robust QEF can be developed based on the noise and detection characteristics of the sensor physics. Once a QEF has been designed, emulated signals, characteristic of the targets, can be iteratively injected into the signal data to be tested. Any fragment of target signature present in the incoming data, above the pre-specified limit of detection (LOD) can yield a resonance event when interfered with a QEF. QRI employs wave equation dynamics, such as the time evolution equation of a Spin-Boson (S-B) bi-stable system, as the underlying model for clutter detection.

The tunneling or interwell transition rate is a computational observable for the S-B dynamics simulation. In an S-B dynamics simulation, the bath temperature is varied to change the tunneling rate. From an algorithmic perspective, noise can be added to the system to simulate bath temperature changes and to modulate the properties of the system. An S-B system can exhibit quantum stochastic resonance phenomena where the signal-to-noise ratio (SNR) of the output signal is maximized. Within QRI, the dependent variable in the governing differential equation, namely the variable out of which the output (processed) signal is extracted, represents quantum amplitudes and probabilities. In some implementations, a semi-classical approximation is employed, whereby the quantum dynamical equations reduce to coupled ordinary differential equations for the interwell instantaneous transition rates, as well as other, uniquely quantum dynamical entities called coherences. This approximation can yield a variety of injected noises due to the interplay of interwell tunneling in a bi-stable S-B system, and the normalization, which, when optimized, can result in a high SNR gain factor.

The governing equations of the QRI are linear in the dependent variables, and do not require an explicit injected noise term (additive or otherwise). The nonlinearity can enter through the way in which the input signal modulates the dynamics and the injected noise, can enter through a relaxation time, or times, stemming from quantum decoherence due to interactions of the quantum system with its environment, which thus effects a partial quantum measurement upon the system. Another way in which noise can be injected can be via a quantum friction, where the quantum friction can be induced by the interaction of the quantum system but its environment. The complex concepts of noise injection can be expressed in terms of matrix vector operations using transformations and quantum trajectory approximations, and implemented using digital processors.

FIG. 1 depicts a schematic of a QRI system 100 including a QEF 105 interferometrically coupled with incoming preconditioned sensor data 110 using an interferometric coupler 115 to detect weak signals buried in noise. The incoming input data can include single or multiple modality data, e.g., spatial, temporal, spatio-temporal, symbolic, spectral, spatio-spectral, audio, video, RF, and the like. The incoming input data can be derived from one or more detector elements. The resulting data (enhanced result 120) can be used to identify one or more events of interest within the incoming data that might not otherwise be identified without the interferometric coupling.

QRI solution development can include two stages: a design stage and an operational stage. The design stage can focus on QEF development for a pre-characterized platform, analyzing noise in the acquired data set using calibrated reference samples, and designing a noise model based on the sensor and background noise analysis. The operational stage can include utilizing the QEF developed in the off-line design phase to computationally enhanced signals and data acquired and the pre-characterized platform in samples other than the reference samples used for a QEF development. The system can include a QRI engine, which can further include a preconditioner to transform the incoming data to a spectral representation and to further transform the spectrally converted data to be compatible with a predetermined dynamical system. The QRI engine can further include an interferometric coupler to combine all the preconditioned output data with a predetermined expresser function, a resonance detector to detect one or more events of interest within the control the output data, and a quantitator to associate a measurement magnitude with each detected event of interest.

Figure 2:
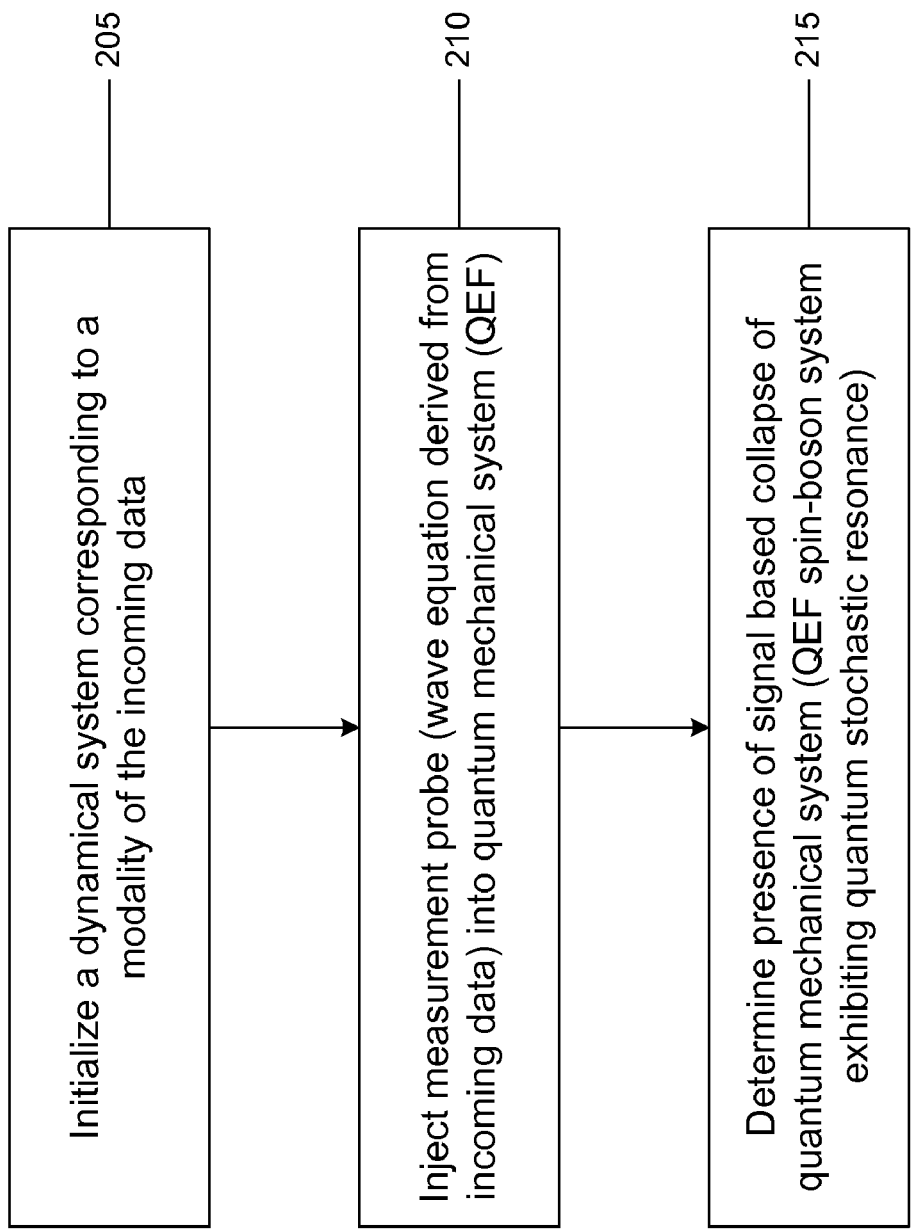
FIG. 2 is a flow chart of a process for causing the collapse of a quantum mechanical system.

FIG. 2 depicts a schematic of a flow diagram illustrating a process by which an injection of a measurement probe can cause a quantum mechanical system to collapse. The received incoming unknown data can be used to initialize a dynamical system corresponding to a modality of the incoming data at 205. The initialized dynamical system can be used to generate a measurement probe which can then be injected into a quantum mechanical system, e.g., the QEF at 210. Subsequently, it can be determined whether the injection of the measurement probe derived from the unknown input data into the quantum mechanical system results in a collapse of the quantum mechanical QEF system at 215. If such a collapse is detected, a presence of signal within the incoming data can be determined.

Figure 3:
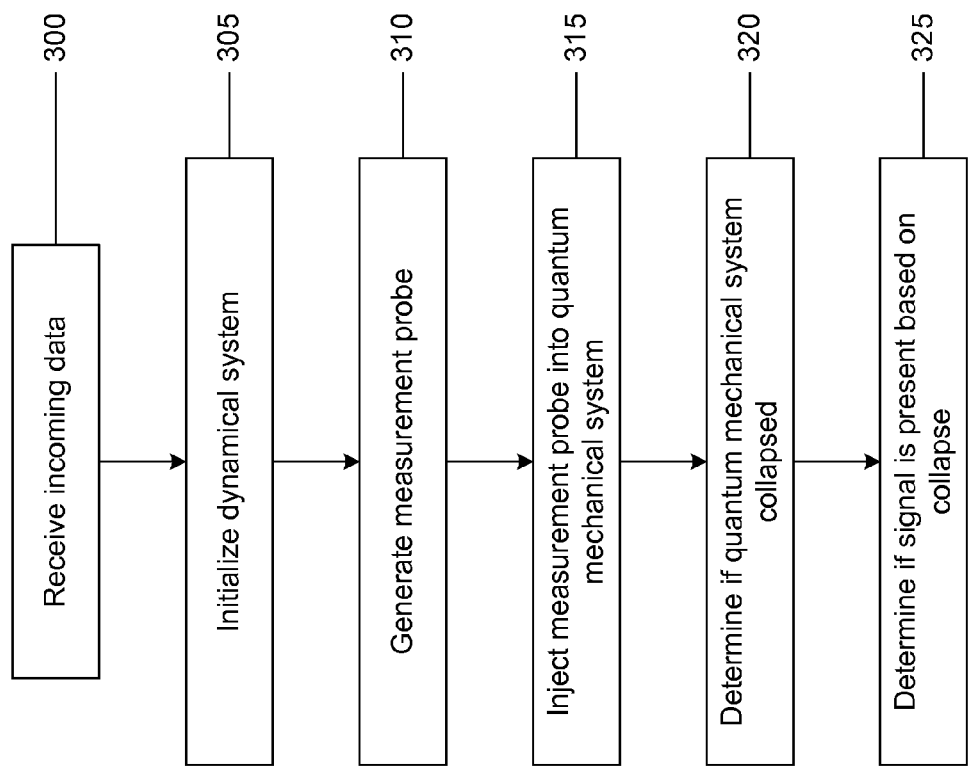
FIG. 3 is a flow chart of a process for using QRI to determine the presence of a signal in incoming data.

FIG. 3 depicts a flow chart of a process for using QRI to determine the presence of a signal in incoming data. The incoming data can be received at 300 and the dynamical system, e.g., S-B dynamical system, can be initialized at 305, e.g., using a trajectory of the dynamical system that corresponds to a modality of the incoming data. Measurement probes can be generated at 310, where the generation of the measurement probes (derived from incoming data) can based, e.g., on a modification of the trajectory of the dynamical system. The measurement probe can be injected into the quantum mechanical system at 315. For example, the measurement probe can be repeatedly injected for a number of iterations. A collapse of the quantum mechanical system can be detected at 320, and, based on the collapse of the quantum mechanical system, the presence of a signal can be detected at 325. In some implementations, the magnitude of the signal can be based on an amount of time between injection of a measurement probe and the collapse of the quantum mechanical system, as captured by the number of interferometric injection iterations.

Figure 4:
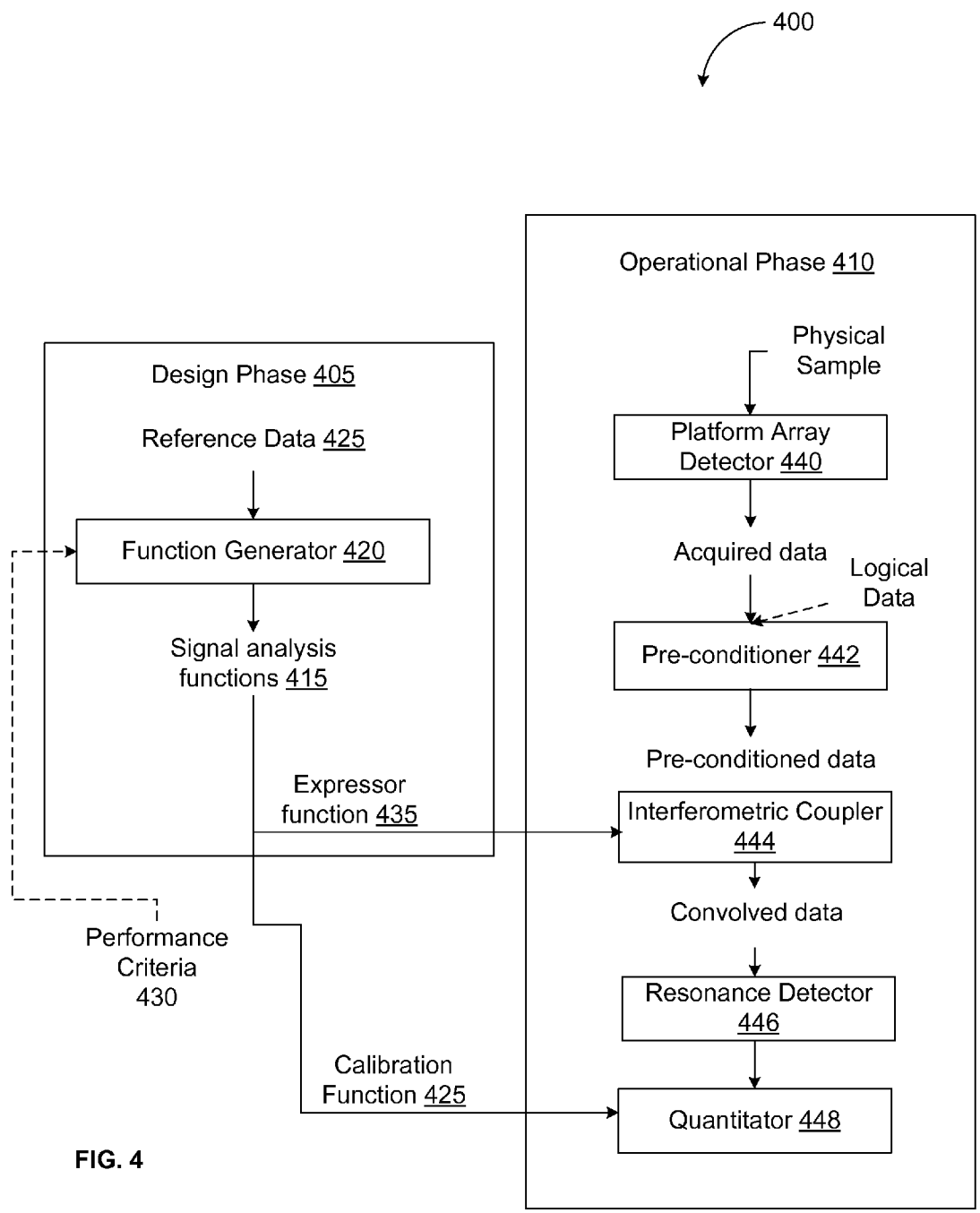
FIG. 4 is a schematic of a QRI engine for signal analysis.

FIG. 4 depicts a schematic of a QRI engine 400 for signal analysis. The system can be divided into a design phase 405 and an operational phase 410. In the design phase 405, signal analysis functions 415, e.g., the QEF, generated by a function generator 420 are determined for a particular experimental platform that is used in the operational phase 410. The QEF signal analysis functions 415 are used in the operational phase 410 by an interferometric computational system to analyze events of interest, e.g., physical samples, a data stream mining, and the like. The events of interest can be associated with the particular sensor platform. In the operational phase 410, a large number of data sets can be analyzed that are derived from the particular platform using the same QEF. A single noise model or QEF can be used for each sensor to achieve a pre-specified LOD. The QEF need not be related to the number of targets of interest. The QEF development protocol can utilize a small number of backgrounds and representative targets for training and optimizing the QEF for a given sensor. Once a QEF has been developed, it can be applied to detect one or more targets within the operational data derived from the sensor. Specification of a new LOD by the user may require a new QEF to be developed. For each new sensor platform, as well as for modifications to an existing platform, a new QEF can be generated or existing QEF's can be altered.

In the design phase 405, a function generator 420 can receive a reference data 425. The reference data 425 can include platform data that categorizes a platform in which the physical samples are analyzed. The platform data can include platform calibration data and platform array characteristics associated with the events of interest. The reference data can also include calibration data that are generated by known events of interest in the particular platform. For example, the calibration data, e.g., calibration function 425, can include data that is acquired in the platform from a set of specially prepared physical samples. The function generator 420 can also receive performance criteria 430 which can establish desired target specifications such as LOD, and limit of quantitation, precision, resolution, specificity, accuracy, SNR, and the like. Based on the reference data, the function generator 425 can generate the signal analysis functions 415. The generated functions can include expressor functions 435 for interferometric signal analysis, such as QEFs and stochastic resonance functions. Details regarding signal analysis using QEFs and stochastic resonance functions and their generation can be found in U.S. Pat. No. 6,142,681 (Title: Method and apparatus for interpreting hybridized bioelectronic DNA microarray of patterns using self-scaling convergent reverberant dynamics; Inventor: Sandeep Gulati; Date of patent: Nov. 7, 2000) and U.S. Pat. No. 6,136,541 (Title: Method and apparatus for analyzing hybridized biochip patterns using resonance interactions employing quantum expressor functions; Inventor: Sandeep Gulati; Date of patent: Oct. 24, 2000); the entire contents of both patents are incorporated herein by reference. The expressor functions 435 can be based on how a dynamical system responds to excitations that are correlated with a signal to be enhanced or with a noise that is typical in the platform. The signal analysis functions 415 can also include calibration functions 425 for quantitating signals that are detected in the acquired data.

The operational phase 410 can involve a platform array detector 440 receiving a physical sampled to produce acquired data. The operational phase 410 can also involve a pre-conditioner 442, an interferometric coupler 444, a resonance detector 446, and a quantitator 448. The platform array detector 440 can acquire data from the physical sensor, such as a CCD array or laser scanner. The acquired data can be sent to the pre-conditioner 440, which can pre-process the acquired data. For example, the pre-conditioner 442 can filter the acquired data and convert the filter data into a spectral domain. Details regarding techniques for converting the signal pattern to a spectral domain are described in U.S. Pat. No. 7,006,680 (Title: System and method for characterizing microarray output data; Inventor: Sandeep Gulati; Date of patent: Feb. 28, 2006), the entire contents of which are incorporated herein by reference. The interferometric coupler applies the QEF defined by the function generator to calculate responses of the corresponding non-linear dynamical system to excitations defined by the driving force spectrum. The resonance detector 446 can process convolved data to identify particular events of interest that can appear within the convolved data. Based on the identified events, the resonance detector 444 can detect if a signal is present in the acquired data. Due to the signal enhancement in the interferometric coupler 444, signals can be detected in the convolved data even if noise is several magnitudes, e.g., ten to thousand times and more, larger than the signal in the acquired data.

Figure 5:
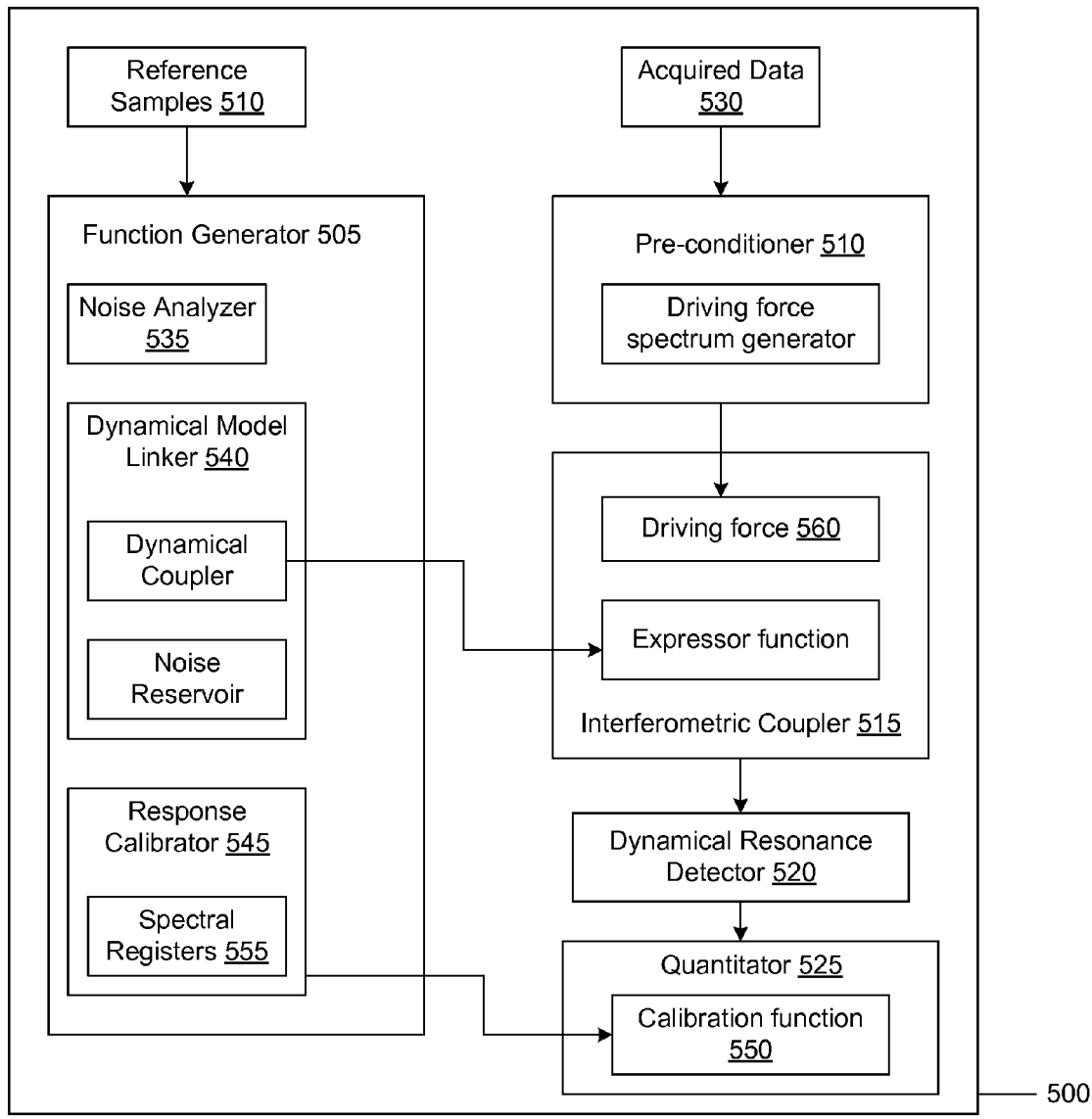
FIG. 5 is a schematic of an example of a QRI engine.

FIG. 5 depicts a schematic of an example of a QRI engine 500. The QRI engine 500 can include a function generator 505 in the design phase to process reference samples 510. Further, the QRI engine 500 can include a pre-conditioner 510, and an interferometric coupler 515, a dynamical resonance detector 520, and a quantitator 525, in the operational phase, to process acquired data 530. The reference samples 510 and the acquired data 530 can correspond to the experimental data acquired on the same pre-characterized sensor platform. The pre-characterized platform can include biomolecular, biomechanical, optical, ionic, optoelectronic, radio frequency, or electronic microdevice platforms. Reference samples 510 can include no-signal samples, false-signal samples, and true-signal samples. In the design phase, the function generator 505 can generate QEF and calibration functions for signal analysis based on the reference samples. The function generator 505 can include a noise analyzer 535, a dynamical model linker 540, and a response calibrator unit 545.

The noise analyzer 535 can pre-process and analyze noise in the reference samples 510. The pre-processing can include data re-sampling and application of passive filters. The oversampling can be performed using interpolation techniques, such as zero padding of high-frequency components. Special purpose filters can be used to decrease high-frequency stochastic noise and to sharpen features of interest. Details regarding these special-purpose filters can be found in the publication titled "Scattered data fitting using a constrained Delaunay Triangulation," (R. J. Renka and A. K. Cline, IMACS Transactions on Scientific Computing 91, AI, Expert Systems, and Symbolic Computation, vol. 3, North Holland, 1992), the entire contents of which are incorporated herein by reference. The noise analyzer 535 can analyze fluctuations in the reference samples 510 using a spectral (Fourier) representation, serialize the acquired data points according to a predetermined scheme and Fourier transform the serialized data to generate a frequency spectrum of the sensor noise. The noise analyzer 535 can identify typical noise, e.g., noise signature, in the pre-characterized sensor platform based on frequency spectrum in no-signal or false-signal reference samples. The noise signature can be identified by comparing frequency spectrums of feature probes in no-signal samples, and identifying portions of the frequency spectrum that have small fluctuations. A tolerance can be computed for identifying the noise signature. The tolerance can specify the allowed sensor probe-to-probe fluctuations in the noise signature, and can be based on design parameters, such as an optimal number of frequency components in the noise signature, a limit arranged for signal detection. False-signal reference samples can be used to identify noise signatures for probes where the false signal, e.g., clutter, modifies the noise spectrum.

Figure 6:
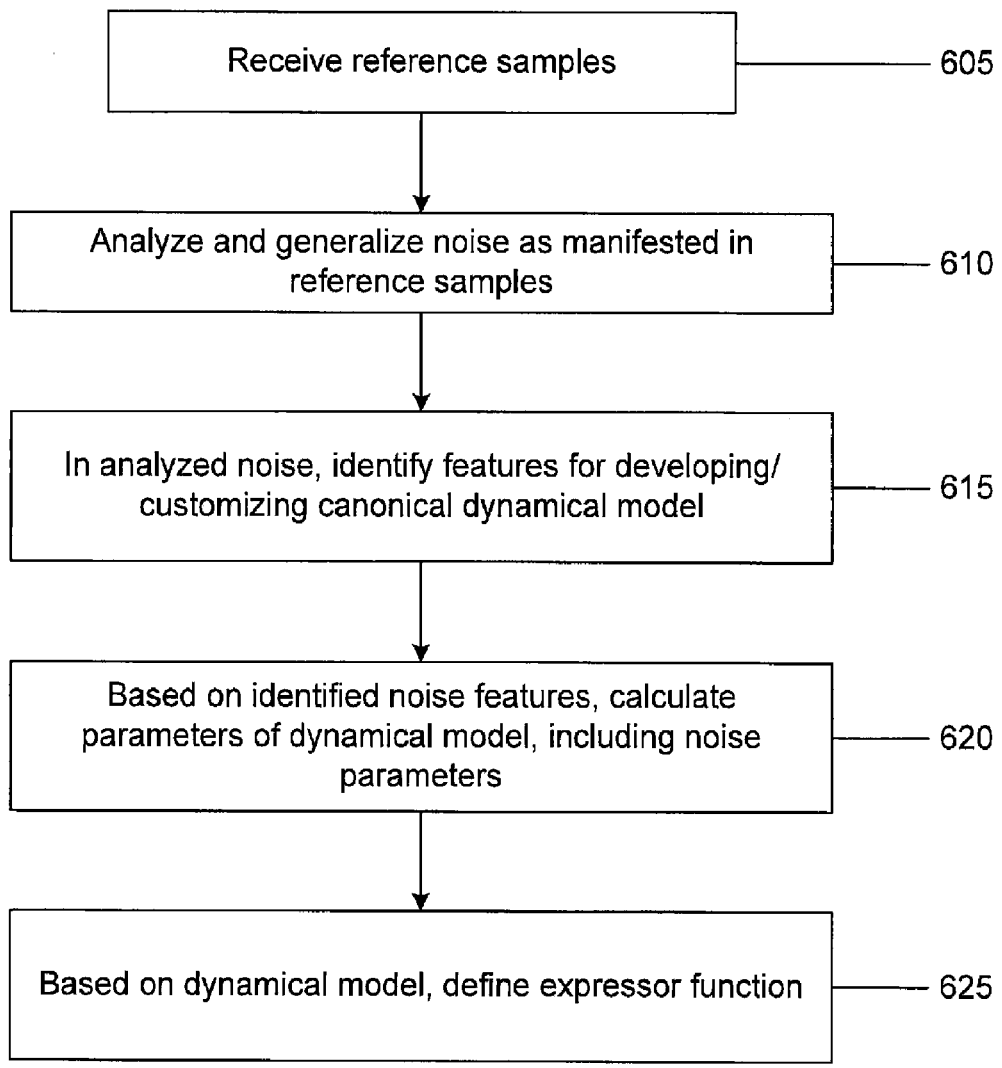
FIG. 6 is a flow chart of a process for generating QEF to drive active signal analysis.

FIG. 6 depicts a flow chart of a process for generating QEF to drive active signal analysis by the customization of Spin-Boson quantum mechanical dynamical system. The reference samples can be received (step 605), e.g., by the function generator. The noise manifested in the reference samples can be analyzed and generalized (step 610), e.g., by the function generator. Target as options can be used to derive a data core for the sensor. The data core can be a portion of the acquired sensor data corresponding to resolution of a feature of interest. For a probe corresponding to a spot in a microarray, the data core can be defined by a circular regions surrounding pixels that represent the spot in a scanned image of the microarray. The data core can define the data that will be used in any further analysis of the probe. The data core can be defined based on a sensor designed layout or user input. The size of the data core can be optimized based on the amount of information required for desired resolution and detection limits for the probe, e.g., by the function generator. For each data core, a sequence of data points can be generated, e.g., by the function generator, from the acquired or preprocessed data in the core according to a preselected serialization scheme. The generated data sequence can then be transformed into a spectral domain using 1-D, 2-D or n-D FFT and characteristic features in the analyzed noise can be identified. In this manner, features for developing and/or customizing a canonical dynamical model in the analyzed noise can be identified (step 615). For example, the function generator can identify features that are typical to noise in the pre-characterized platform but change if a signal is present. The identified noise features can be used to customize the canonical dynamical model (step 620). Parameters of the canonical dynamical model can be calculated based on the identified noise features. The canonical dynamical model can be used to enhance signals that are below the nice fellow. For example, the dynamical model can be designed such that it responds differently to different excitations. In particular, certain responses can be smaller for excitations that correspond to the identified noise features and larger for excitations that correspond to signals. Thus, in these responses, the dynamical model choice can enhance the signals relative to the noise level.

The dynamical model can include a nonlinear dynamical system, such as a bi-stable system, and a noise reservoir coupled to the nonlinear system. The noise reservoir and the coupling to the nonlinear system can be designed based on the noise features identified in the reference samples. The noise reservoir can be represented by a stochastic force coupled to the nonlinear system, and parameters of the stochastic force can be designed according to the identified noise features. A dissipative dynamical model wherein the energy is dissipated from the system, e.g., by stochastic forces, can be employed. The function generator can match the spectral properties of the dynamical model and the noise features identified for the noise signature. The nonlinear dynamical system is coupled to a noise reservoir that includes frequency components corresponding to the identified noise feature. The function generator can select couplings between the noise reservoir and the nonlinear system to match the spectrum of fluctuations, e.g., noise, in the nonlinear system with the spectrum of the identified noise features. For example, the fluctuation spectrum of the nonlinear system can be calculated or measured for different couplings, and compared to the noise features based on the comparison, the couplings can be varied until a matching criterion is met.

In addition, the function generator can set some parameters of the nonlinear dynamical system using calibrated true signal samples. To achieve a desired resolution or LOD for signal analysis, the response of the nonlinear dynamical system can be calculated for excitations corresponding to different signal levels according to the calibrated samples. The responses to the different signal levels can be compared to the response when no signal is present to verify whether the desired resolution or limit of detection can be met with the dynamical model. If not, parameters of the dynamical model can be adjusted to reach an optimal resolution or LOD. The function generator, thus, defines a QEF based on the dynamical model and the noise signature of the platform that QEF intern characterizes the response of the dynamical model to an excitation (step 625). The response of the dynamical model and its final state can be determined by interferometrically coupling the QEF to the excitation.

FIGS. 8A-8D illustrate amplitude versus frequency spectra in which selected windows of such spectra can be used to generate a noise reservoir. In reference 1, as illustrated in FIGS. 8A-8D, the Windows identify sections of spectra that are sensitive to changes in concentration and may be utilized to determine a sensitivity of regions of spectra. Higher order statistical operators including by spectral and try spectral measures can be computed to determine properties of the regions of the spectra. The regions of frequency spectra that are of interest are determined by transforming the spectra and to spectral energies that can be associated with the specific events of interest are classified as signal and noise. Subsequently, it can be determined which regions of frequency spectra are most representative of noise and/or background and/or which spectral regions are most vulnerable to background interference so that they may be eliminated from modeling. The selected spectral regions may then be validated using calibrated nonspecific data. The spectral regions that are most representative of noise may be used to generate/form the noise reservoir. Energy asymmetry between spectral energy of regions deemed to be most characteristic of signal and spectral region's most representative of noise can then be computed to initialize transition rate equations for the bi-stable model.

Calibrated reference samples can be used to determine if energy asymmetry is adequate to produce an observable tunneling rate when conditions of quantum stochastic resonance are met. A qualitative difference in tunneling rate must be observed and known examples of signal and no signal incoming data are introduced in the system. A statistically significant change in tunneling rate, e.g., greater than or equal to two standard deviations over the root mean square (RMS) noise in tunneling rate when incoming data is only noise is sufficient to conclude that a qualitatively different tunneling rate is observed. A less stringent statistical criteria may be used if the magnitude of the average tunneling rate is greater than one for a particular data modality. If the energy asymmetry is inadequate to produce a qualitative change in the observable tunneling rate between signal and noise, synthetic resampling techniques, such as Renka Cline algorithm, convolution with the wavelet kernels, and the like, can be used to generate additional spectral harmonics in the incoming data and the above steps can be repeated. If a qualitative change in tunneling rate is observed, then a resonance event is detected.

An example for identifying noise signatures and for selecting frequency components for the noise reservoir entails transforming the incoming data modality into a spectral routine through Fourier transforms. The transformed data is then analyzed to determine the periodic city of different spectral windows using different combinations of spectral harmonics. When spectral regions at identified with the different PID cities corresponding to signal and noise examples, then these regions are used to compute the spectral energies to determine the energy asymmetry for initializing the bi-stable system dynamics. The noise reservoir and its interaction with the dynamical system are designed to quickly absorb noise in a choir data to be analyzed.

The noise analyzer can also analyze noise in true-signal samples using the same techniques as for no-signal or false-signal samples. The my spectrum can be different for true-signal samples when compared to that for no-signal or false-signal samples. The noise spectrum of the true-signal samples can also depend on the strength of the signal. Such dependencies can be analyzed using calibrated samples, and the result of the analysis can be used for signal quantitation. The analysis of calibrated samples can also be used to set design parameters such as a lower or upper signal limit for which the signal detection is planned. The dynamical modeling career can compute a QEF based on the noise signature and the design parameters. The QEF can describe a response to an excitation of a canonical nonlinear by stabile dynamical system. The nonlinear dynamical system is coupled to a noise reservoir by a dynamical coupler. The noise reservoir has a frequency spectrum that is based on the noise signature identified by the noise analyzer. The dynamical coupler is defined such that, if the nonlinear dynamical system receives an excitation who spectrum corresponds to the noise signature of the sensor platform, the excitation energy is quickly absorb and the noise reservoir through the dynamical coupler. If the spectrum of the excitation is different from that of the noise signature of the platform, the noise reservoir can be slow to absorb the excitation energy. The excitation may even qualitatively change the state of the nonlinear dynamical system.

Due to the slow DK of the excitation energy, and the excitation includes a signal who spectrum is different from that of the noise signature of the platform, the signal can be enhanced. If the excitation also includes and noise component of the sensor platform, the signal can be enhanced because the noise is quickly absorbed in the noise reservoir. The signal enhancement depends on parameters of the dynamical system. The dynamical modeling Kurt can set these parameters to optimize the enhancement or to achieve a particular limit of signal detection.

Figure 9:
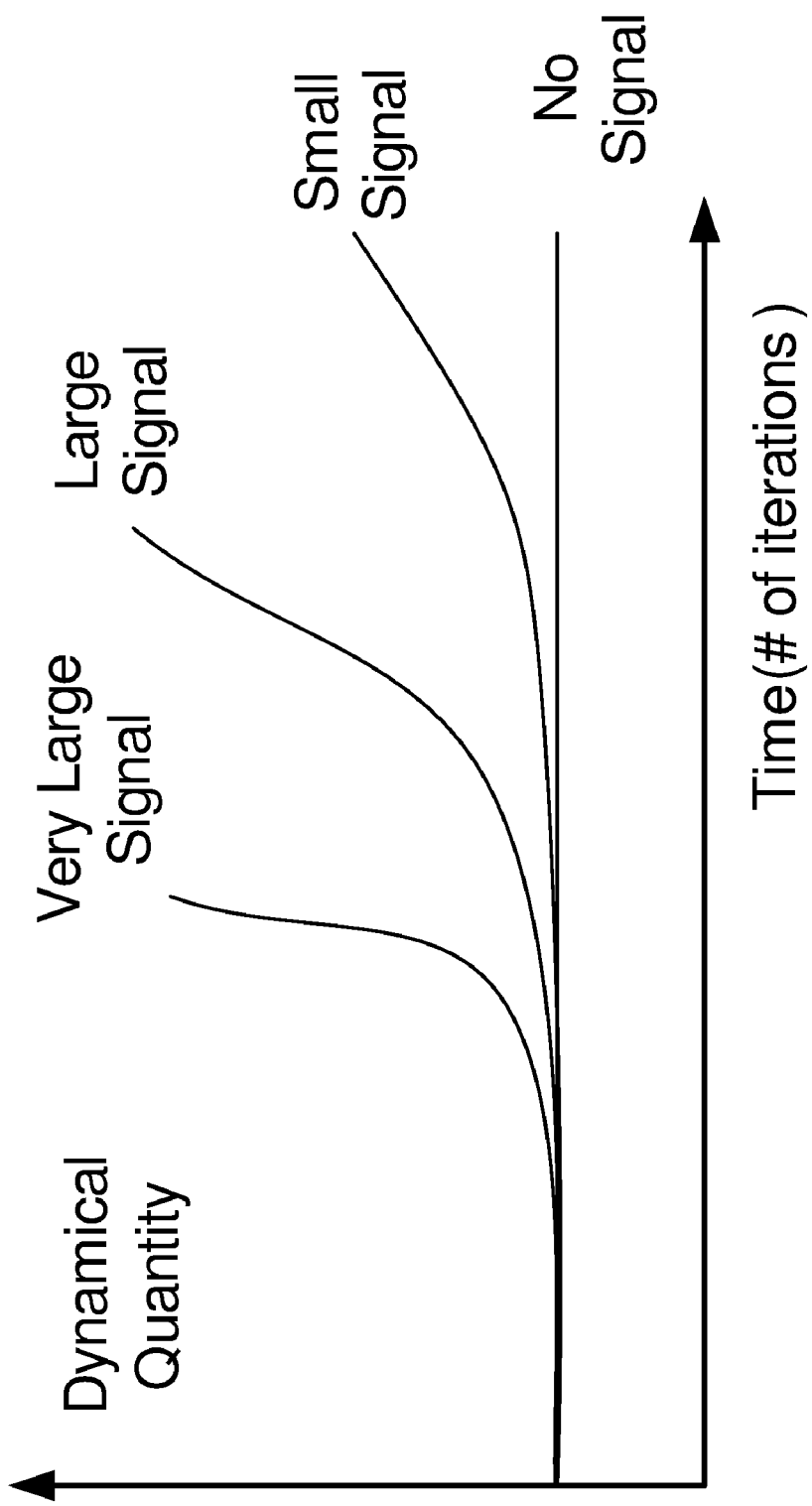
FIG. 9 is a schematic of a diagram for detecting signals using the expressor function.

FIG. 9 depicts a schematic diagram illustrating a dynamical model for signal analysis. Since QEF can be used to calculate the system's response to excitation, it can be used to actively and hands signals. For some systems, such as a Spin-Boson model described, the expressor function can be explicitly calculated. As illustrated in FIG. 9, a S-B quantum doubled system dynamical model can be used to generate expressor functions for signal analysis. The dynamical model can include a two-state (bistable) system and a noise reservoir coupled to the two-state. The two-state system can also be subject to a driving force that can and use transitions between the two states of the system. The two-state (bistable) system has certain characteristics that show a noise invariance. Excitations (n) that are similar to the noise from the noise reservoir cause negligible change to a characteristic noise (N). However, if an excitation includes signal (S) within amplitude that is about the same or larger than a small threshold ($\epsilon$), the state of the system and a characteristic noise N substantially change. For example, the signal interferes with the noise. Stating this schematically according to the system:

n+N is similar to N, but $\epsilon$S+N is not similar to N

For example, the noise in the two-state system can be characterized by a typical transition frequency ($F_0$) between the two states of the system. If the system receives excitations including both signal, with an amplitude ($\delta$), and noise N, the transition frequency depends essentially only upon the signal, e.g.:

$F_0[\delta S+N] \rightarrow F_0[\delta S]$

By repeatedly exciting the system, the signal portion, $\delta S$, can be accumulated to reach that threshold level, $\epsilon$, while the noise, N, is mostly absorbed in the noise reservoir. At the new threshold level, $\epsilon$, a resonance can occur and the system can change its state. In the new state, the characteristic frequency, $F_0$, starts to change its value at a different rate for the repeated excitations. The rate change allows detecting the residents. After a number of excitations, if the rate has not changed, no signal is present, and if the rate has changed, the signal is present. The two state system is a nonlinear dynamical system that has an "|UP" state and a "|DOWN)" state separated by a barrier. The system can make transitions between the |UP) and |DOWN) states. Such transitions can depend on a barrier height between the two states and the energy level in the two state system. This energy level can change to energy transfer to and from the noise reservoir and due to the driving force.

In a physical phenomenon called stochastic resonance (SR), a periodic signal can be enhanced using a nonlinear dynamical system similar to the two state system. In stochastic resonance, the periodic signal can be enhanced by increasing a noise level in the system. The noise can be a stochastic noise, such as Gaussian white noise. The periodic signal can be included in the driving force at amplitude that is insufficient to in use transitions through the barrier separating the two states. For noise levels that are substantially smaller than the energy barrier, essentially no transitions are and used between the two states. On the other hand, for noise levels that are substantially larger than the energy barrier, the transitions can be driven entirely by the stochastic forces of the noise, independent from the patriotic signal. In between, the transitions can have both a stochastic component in a complement that is correlated with the periodic signal. Near a resonance level of the noise, the transition complement which is correlated with the signal can become larger than the stochastic component. Thus the periodic signal can be enhanced relative to the noise.

Instead of a fully stochastic noise, the dynamical model can use to noise reservoir that has a design frequency spectrum. The noise reservoir can have a frequency spectrum that is designed to enhance signals other than patriotic signals. For example, the noise reservoir can have a frequency spectrum that corresponds to noise that is typical in a particular type of experiment. If the two state system is driven by a driving force that includes no signal but the typical experimental noise, the driving force just adds the same type of noise that the system already receives from the noise reservoir. Thus, the system has dynamics corresponding to an increased noise level from the noise reservoir. On the other hand, if the two state system is driven by a driving force that includes both a signal and the typical noise, the signal can be enhanced by selecting a resonance level for the noise received from the noise reservoir. Thus, near the resonance level in the system, the signal can induce dynamics that is qualitatively different from the dynamics corresponding to the increased noise level. The signal can be detected by characterizing the dynamics of the system in response to excitations, such as driving forces.

There is a tendency of the dynamic model to preserve equilibrium of transition right, e.g., left to right and right to left transitions, between the two minimum. With such an arrangement, incoming data is transformed to a driving patriotic force. If the incoming data is solely comprises noise, then it cannot be stripped equilibrium. However, if incoming data contains signal, e.g., signal associated with an event of interest, it will disturb equilibrium between the two transition rights. Such disturbances in equilibrium transition right are an indicator of signal strength as and by deed in the different periodicity structure between signal and noise. If it is a large magnitude signal, it will rapidly settle in many computer iterations. Also, large signal can cause high or infinite tunneling rate, small signals can exhibit slow tunneling rate, or small signals can stop tunneling from occurring completely. In general, high noise can increase average tunneling rate. A comparison of changes in tunneling rate between injected noise and incoming data can be determined. Thereafter, using calibrated samples, differences in tunneling rate may be determined to facilitate distinguishing signal from noise.

In some implementations, the dynamical model is a quantum model in which the two state system and the noise reservoir are described by half spent operators (Pauli matrices) and quantum oscillators (Bosons), respectively. Quantum oscillators can have only discrete energy values, e.g., they can be quantized. The quantum oscillator can have excitations that behave as Bosons, as opposed to fermions, because multiple excitations can be in the same quantum state, while only one fermion is allowed in one quantum state. Spin operators, in general, described a spinning quantum object. The spin operators described a spin vector about which the object is spinning. The spin vector has a length that depends on the rotation rate. While a classical object's spin vector can point in any direction and can't have any length, a quantum object's spin vector can have a length that takes only discrete values. The shortest length is a half spin on the scale of the Planck constant. In addition, quantum spin vectors can have only two possible directions relative to a coordinate axis: up or down.

Accordingly, in the dynamical system, the |UP⟩ and |DOWN⟩ states are defined as quantum states. These quantum states define a phase space of a spin operator having an x-component, $\sigma_x$, a y-component, $\sigma_y$, and a z-component, $\sigma_z$. The z-component, $\sigma_z$, can be used to represent energy differences between the |UP⟩ and |DOWN⟩ states, because $\sigma_z$ has different eigenvalues for the two states, e.g., +/−1, $\sigma_z$ |UP⟩ = |UP, $\sigma_z$ |DOWN⟩=−|DOWN. The x-component, $\sigma_x$, induces transitions between the two states; $\sigma_z$ |UP⟩=|DOWN⟩), $\sigma_x$ |DOWN⟩=|UP⟩. Therefore, the two state system can be described using the $\sigma_z$ operator to specify an energy difference, $E_0$, between the |UP⟩ and |DOWN⟩ states. The driving force, f(t), can be added to modulate the energy difference. An effective barrier between the two states can be represented by the $\sigma_x$ operator whose coefficient, D, corresponds to a transition frequency between the two states. Thus, the two state system can be represented by a spin Hamiltonian, $H_s$, as:

$$H_s = (E_0 + f(t))\sigma_z + D\sigma_x$$

The noise reservoir can be represented by a Boson Hamiltonian ($H_B$) describing noise that is generated by multiple quantum oscillators, where each oscillator has a characteristic frequency, $\omega$, and has an energy described by a corresponding Boson operator, $b_\omega$, which decreases the oscillator's energy, and its conjugate, $b_\omega^+$, which increases the oscillator's energy as:

$$H_B = -\Sigma_\omega \omega \beta_\omega^+ \beta \omega + \text{constant}$$

The frequency spectrum of the noise reservoir is determined by the characteristic frequencies of the quantum oscillators and the reservoir's interaction with the two state system. In the noise reservoir, each oscillator is coupled to the z-component, $\sigma_z$, of the two state system with a corresponding coupling, $K_\omega$, according to an interaction Hamiltonian, $H_I$, as:

$$H_T = H_S + H_B + H_I$$

If there is no driving force, the two state system can be in an asymmetric mixed quantum state in which the |UP⟩ state has a smaller weight than the |DOWN⟩ state. Between the |UP⟩ and |DOWN⟩ states, transitions occur with some probability. These transitions have a characteristic frequency, $F_0$, that depends on the parameters, $E_0$, and D of the spin Hamiltonian and the couplings between the spin and Boson Hamiltonians. These parameters and couplings can be selected such that the asymmetry of the state and the characteristic frequency, $F_0$, are essentially stable for a preselected range of a total energy in the model. From a statistical point of view, the range of the total energy corresponds to a temperature range.

If the two state system receives an external excitation, such as the driving force, the two state system changes its asymmetric state to a new quantum state. If the driving force includes a noise component that is similar to the noise received from the noise reservoir, the driving force increases only the noise level and the temperature in the two state system without substantially altering the asymmetry of the state or the characteristic frequency, $F_0$. However, if the driving force includes a signal component that is different from the noise from the noise reservoir, the new quantum state can be substantially different from the asymmetric quantum state that corresponds to no signal. For example, the new quantum state may become more symmetric or the characteristic frequency, $F_0$, may change because the signal has a weak coupling to the noise reservoir. The substantial change of the quantum state in response to signals is referred to as quantum resonance interference. The coupler is an interference coupler that is a generalized computational unit that implements the interference between QEF and wave-transformed raw data. The two computational entities actually are two mathematical systems exhibiting QSR phenomena. The interference engine couples these two systems together mathematically and evaluates the result. The wave-wave interaction implemented within the interference process emulates the physical energy transfer principle that is basic to active hardware devices.

The following mathematical steps are performed by the interferometric coupler using the preconditioned signal pattern:

$T^{(0)}$ is defined as a vector containing the preconditioned components from an event of interest, and $T^{(i)} = T^{(i-1)} \overline{Q}^{(i)}$ where $Q^{(i)}$ represents is the QEF after i convolutions.

Thus, $$\bar{f}^{(1)} = \bar{f}^{(0)} \bar{Q}^{(1)}$$

$$\bar{f}^{(2)} = \bar{f}^{(1)} \bar{Q}^{(2)} = \bar{f}^{(0)} \bar{Q}^{(1)} \bar{Q}^{(1)}$$

where $\bar{Q}^{(0)}$ represents the QEF developed in the preceding step and (its dimensionless quantity), and where $\bar{Q}^{(i)}$ represents the i-th perturbation to the QEF, induced by perturbing one of its spectral components.

for k=1 to n
   for j=1 to 1000 (set to a large counter value)
   perturb the $k^{th}$ component of QEF as below $$Q^j(k) = [Q^{j-1}(k) + jC_1 \sin(w_0 j + C_1)]^+$$

where $$[x]^+ = \begin{cases} x & \text{if } x \geq 0 \\ 0 & \text{if } x < 0 \end{cases}$$

and $$C_1 = \frac{1}{3}\left(\frac{2\alpha}{360}\right); \alpha \text{ denotes a small constant;}$$

Let $w_0$=the variance computed from the values $$\frac{\bar{f}_{pc}}{\text{Max}(\bar{f}_{pc})}$$

where $f_{pc}$ denotes the preconditioned spectral vector corresponding to a known event of interest present in the arrayed pattern being analyzed.

As an example, $f_{pc}$ refers to the spectral components of the positive control.

Global QEF iterations may be performed if monotonic divergence is detected between the preconditioned extraction core being analyzed and the canonical negative control, then the same convolution coupling operations are repeated for all the spectral harmonics. The global QEF iterations are provided by:

Set $\bar{f}^0 = \bar{q}^{(j+2)}$

For m=1 to 25 (chosen to be a small count value)
Compute $$\bar{f}^m = \bar{f}^{m-1} + (m+j)C_1 \sin(\omega_0(m+j)+C_1) + mC_2 \sin(\omega_{1m}+C_2)$$

where $w_1$ captures the variance of the components of $$\frac{\bar{f}_{Nc}}{\text{Max}(\bar{f}_{Nc})}$$

$$C_2 = C_1 + \varepsilon\left(\frac{\text{Parseval Avg from Pos. Con. PM}}{\text{Parseval Avg from Neg. Con PM}}\right)$$

The convolution iteration can be expressed as:

$$R_{kj} = \frac{\bar{f}^{(j-1)} \cdot \bar{Q}^j}{f_{nc}^{(j-1)} \cdot \bar{Q}^j}$$

where $f_{nc}$ refers to the spectral components of a canonical negative control, or preconditioned footprint an event of interest known to be absent in the arrayed image.

After each convolution iteration check for monotonicity of $$\frac{R_{kj+1}}{R_{kj+1}} > 1$$

AND $$\frac{R_{kj+1}}{R_{kj}} > 1$$

if yes, then exit loop to perform global QEF iterations (that means this particular k component is important, i.e we are diverging from the negative control.)
If no then continue
end j loop
end k loop where Parseval Avg. from Pos. CON. PM refers to the parseval number for a canonical event of interest known to be present, and Parseval Avg. from Neg. Con. PM refers to the parseval number for a canonical event of interest known to be absent.

and $\epsilon$ is chosen to be small, 0.0001.

Again after each coupler iteration compute the term $$R_m = \frac{(\bar{f}^{j+m-1}) \cdot (\bar{f}^m)}{(\bar{f}_{Nc}^{j+m-1}) \cdot (\bar{f}^m)}.$$

Successively compute $R_m, R_{m+1}, R_{m+2} \ldots$

After each convolution iteration check if $$\frac{R_{m+2}}{R_{m+1}} > 1$$

AND $$\frac{R_{m+1}}{R_m} > 1$$

If the conditions of the above test are met, resonance is concluded and event of interest is present.

If the monotonicity test fails, them the preconditioned test pattern is normalized using the expressions below.

if $$\bar{f}^{(j)} - \bar{f}^{(j-i)} > \bar{f}_{pc}^{(g)} - \bar{f}_{Nc}^{(c)}$$

for any component then

-continued
$$\bar{f}^{(j)} = \bar{f}^{(j)} - \left(\frac{\sum \bar{f}^{(j)} - \sum \bar{f}^{(j-1)}}{25}\right)$$

The above assumes an object with 25 spectral harmonics of interest.

The detailed equations for the coupler unit and resonance detector unit are given below:

for j=1 to N $$\Delta j \rightarrow j+1 = \left(\frac{\sum (f_i \cdot \hat{Q}^{j+1,pm})/\sum (NCF_i^{0,pm} \cdot Q^{j+1})}{\sum (f_i^{o,pm} \cdot Q^{j,pm})/\sum (NCF_i^{g,pm} \cdot Q^{j,pm})}\right)$$

$$QEF_{r+1} = (QEF_r + A(j,r) + B/r)$$

where $$B = f(w_1)$$

and $$W_1 = \sigma\left(\frac{\sqrt{PSD_{pm,njc}}}{\sqrt{\text{man } PSD_{pm,njc}}}\right)$$

$$A = \phi_c(j+r) \cdot \{\sin(w_0(j+r) + \phi_c)\}$$

$$B = \phi_{c_1} r \cdot \{\sin(w,(r) + \phi_{c1})\}$$

$$\phi_{c1} = \phi_c + \varepsilon\left(\frac{\sigma_1}{\sigma_2}\right)\{= 0.0001\}$$

$$Q^{j+1} = \hat{Q}^j (j \neq k)$$

$$Q^{j+1} = \left[\hat{Q}^j(i=k) + (\phi_c \cdot j)\sin(w_0 j + \phi_c)\right]$$

$$\text{Check} \frac{\Delta_{j-1,j+2}^2}{\Delta j} > 1$$

$$\frac{\Delta j+1 \rightarrow j+2}{\Delta j \rightarrow j+1} > 1 \; \left| \; \frac{\Delta j \rightarrow j+1}{\Delta j \rightarrow j} > 1 \right.$$

$$\phi_c = \frac{1}{3} \cdot \frac{2\pi}{360}$$

$$W_0 = \sigma\left(\frac{PSD_{QEFpc,pm}}{\max(PSD_{QEF;pc,pm})}\right)$$

$$W_1 = \sigma\left(\frac{PSD_{QEF,NC,pm}}{\max(PSD_{QEF,NC,pm})}\right) \; w_0 \approx w_1$$

Resonant Marker Identification

Finally, resonance marker detector performs the following mathematical calculations using the convolved signal pattern to identify the events of interest within the convolved signal pattern.

The resonant iteration is terminated when $$\frac{\Delta_{j-1,j+2}^2}{\Delta j} > 1$$

$$\frac{\Delta j+1 \rightarrow j+2}{\Delta j \rightarrow j+1} > 1 \; \left| \; \frac{\Delta j \rightarrow j+1}{\Delta j \rightarrow j-1} > 1 \right.$$

or when iteration counter t exceeds preset "N" (e.g., $10^3$ iterations) (for digital approximation to analog dynamics).

Figure 7:
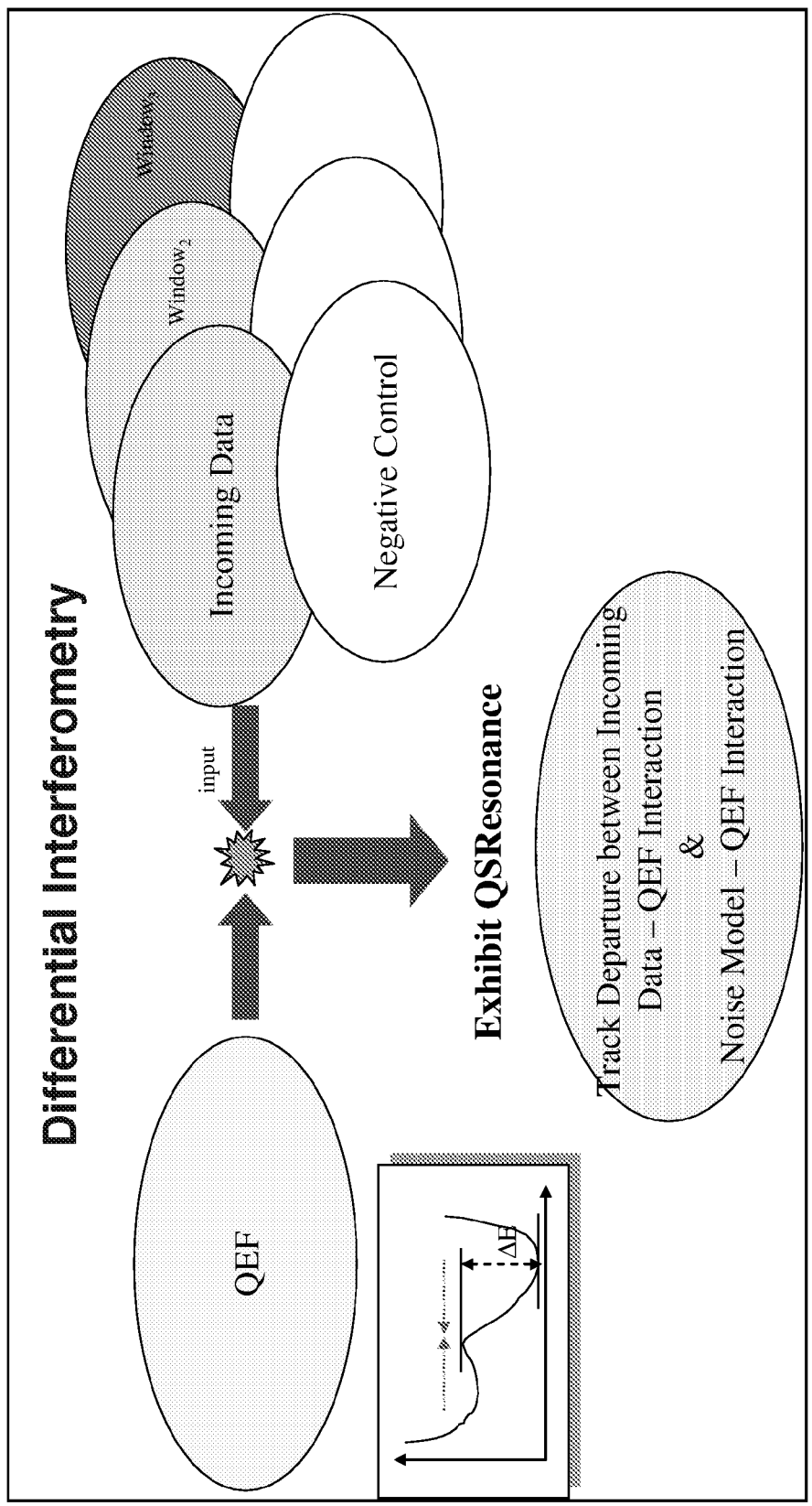
FIG. 7 is a schematic of a differential interference protocol.

FIG. 7 depicts a schematic of a differential interference protocol. QRI allows two protocols within the interference processor, such as interference between QEF and raw data, and differential interference between QEF & raw data and QEF and a pre-specified negative control as illustrated in FIG. 7. This provides significant robustness to false alarms in high clutter situations. The interference iterations are implemented using an iterative control plane that entails a perturbation of QEF after each interference iteration. The perturbation protocol is a function of the desired precision in detection objective. The energy of QEF wave packet is increased in each perturbation. The response calibrator 545 defines a calibration function 550 for signal quantitation. The calibration function 550 describes the relation between a quantity, such as a concentration of an active agent in a sample, and a signal strength that is measured with active signal processing. Specifically, within the QRI formalism the signal strength is measured by resonance amplitude that describes how fast the signal in the sample is enhanced as the quantum expressor function is applied. The calibration function 550 is based on calibrated samples that are true-signal samples exposed to controlled amounts of the active agent. The calibration function 550 uses spectral registers 555. Each spectral register 555 represents concentration range of the active agent, and specifies a spectral feature and corresponding region in the frequency spectrum of a sample. (The spectral register 555 is not limited to the frequencies of the noise signature of the platform.) The frequency regions of the spectral register 555 are selected by comparing the frequency spectrum of the calibrated samples, and selecting the portion of the spectrum that develops the spectral feature if the concentration is in the range corresponding to the register 555.

FIGS. 8A-8D depict illustrations for using a driving force impulse to excite a two-state system that has a coupling to a noise reservoir. The noise reservoir is designed to generate a noise in the two-state system through the coupling such that the generated noise is similar to typical noise in the driving force impulse. When the driving force 560 impulse is applied, energy is injected into the two-state system. The injected energy excites the two-state system and raises its energy. As the excitation decays, the injected energy is redistributed between different degrees of freedom of the two-state system and, due to the coupling, the noise reservoir. After some relaxation time, the system reaches a new state. FIG. 8 above illustrates how the energy of the two-state system changes if a no-signal impulse is applied to the two-state system. The no-signal impulse is a driving force impulse that includes only the typical noise. As the no-signal impulse is being applied, energy is injected into the two-state system. Because the no-signal impulse has only typical noise that is similar to the noise from the noise reservoir, most of he injected energy is absorbed in a short relaxation time ("$T_1$") in the noise reservoir through the coupling. After the injected energy is redistributed in a new state of the system, the energy has been increased by a small amount ("$\Delta E_1$"). The energy increase $\Delta E_1$ corresponds to an increased noise level due to the injected energy. If a no-signal impulse is applied in a second iteration, the two state system may have different relaxation time $T_1'$ and energy increase $\Delta E_1'$ than for the first impulse due to the previous changes in the system.

FIGS. 8A-8D further illustrate how the energy of the two-state system changes if a signal impulse is applied to the two-state system. The signal impulse is a driving force impulse that includes a signal in addition to the typical noise. As for the no-signal impulse, energy is injected into the two-state system as the signal impulse is applied, and the noise reservoir absorbs the portion of the injected energy that represents typical noise in a short time. For the portion of the injected energy that represents the signal, the decay takes a longer relaxation time ("T2"). The injected energy is redistributed in a new state in which the energy has been increased by a larger amount ("ΔE2") than in the case of no-signal impulse. (That is, less energy has been absorbed in the noise reservoir.) The energy increase ΔE2 corresponds not only to an increased noise level but also a characteristic change in the quantum state of the two-state system. If a signal impulse is applied in a second iteration, the two state system may have a different relaxation time T2' and energy increase ΔE2' than for the first impulse due to the previous changes in the system.

The signal can be detected by comparing the system's responses to the signal impulse and the no-signal impulse. For example, the no-signal impulse can be generated by a system similar to the noise reservoir. The system's response can be characterized by a dynamical quantity ("Θ(k)") that is defined for a k-th iteration by a difference between the energy increase ΔE1(k) at the k-th application of a no-signal impulse and the energy increase ΔE2(k) at the k-th application of a signal impulse as $\Theta(k)=\Delta E_2(k)-\Delta E_1(k)$.

Alternatively, the system's response can be characterized by the relaxation time T or any other dynamical quantity that is different if a signal is present. In the operational phase, the acquired data are processed by the Preconditioner. The Preconditioner performs the same preprocessing steps as the noise analyzer. The Preconditioner includes a driving force spectrum generator that generates a frequency spectrum for a force that drives the dynamical system defined by the dynamical model linker. The preprocessed data is Fourier transformed to define a Fourier spectrum, and the force spectrum is defined by selecting those components of the Fourier spectrum that correspond to the frequencies in the noise signature of the pre-characterized platform. The interferometric coupler applies the QEF defined by the function generator to calculate responses of the corresponding non-linear dynamical system to excitations defined by the driving force spectrum. The Dynamical Resonance Detector detects signals in the acquired data based on a qualitative change in a dynamical quantity. The dynamical quantity is calculated based on the data generated by the interferometric coupler.

FIG. 9 depicts a schematic diagram illustrating time dependence of a dynamical quantity in a driven dynamical model for signal analysis. If a signal is detected by the resonance detector, the quantitator uses spectral registers and a calibration function specified by the response calibrator to quantitate detected signal. The quantitator determines resonance amplitude of a detected signal, selects a functional component according to the spectral registers, and uses the selected component of the calibration function to determine a quantitative value for the concentration of an active agent corresponding to the detected signal.

In specific implementations, the dynamical model can include other non-linear dynamical systems, such as quantum systems with more than two states or multiple two-state systems coupled together. Instead of quantum systems, the dynamical model can include classical systems describing the two-state system or the noise reservoir or both. For example, the two-state system can include a double-well potential ("U(x)") in which a classical particle is moving along a direction x. In addition to a force dU/dx from the potential, the classical particle is subject the driving force f(t) and a stochastic force ("N(t)") describing an interaction between the particle and the noise reservoir. The dynamics of the particle is described as $$dx/dt=dU/dx+f(t)+N(t).$$

Similar to the quantum case, a response of the classical system can be different for different excitations in the driving force f. If the driving force includes noise that is similar to the stochastic noise N, only the noise level is increased in the system. If the driving force includes a signal, the signal may be enhanced by stochastic resonance.

FIG. 9 further illustrates how a dynamical quantity ("Θ") changes when excitations are applied to a non-linear dynamical system coupled to a noise bath that is designed according to a typical noise in the excitations. For example, the dynamical quantity can be based on comparing the energy increase in a two-state quantum system in response to no-signal impulses and sample impulses that may or may not include a signal, as discussed above with reference to FIG. 11. The excitations, such as driving forces, can be applied continuously or iteratively in impulses. The presence of the signal can be detected by analyzing the functional form of the dynamical quantity Q as a function of the number of iterations (or time for continuously applied driving forces). If no signal is present in the iteratively applied sample impulses, the two-state system responds substantially the same way to the sample impulse than the no-signal impulse even as the number of iterations is increasing. Accordingly, the dynamical quantity Q is represented by flat curve as a function of iterations/time.

If a small signal is present in the iteratively applied sample impulses, the two-state system responds slightly different to the sample impulse than the no-signal impulse. However, the quantum state of the two-state system is also changed due to the presence of the signal. The change of the quantum states couples back to the response of the system, which becomes more and more different from the no-signal case as the number of iterations is increasing. Due to the feedback mechanism, the dynamical quantity Q departs in a non-linear way from the flat curve of the no-signal case at a critical number of iterations. As the signal's level is increasing relative to the noise in the sample impulses, the critical number of iterations is decreasing. Further details regarding detecting events of interest using QRI can be found in US Patent Publication No. 2006/0053005 (Title: Detecting events of interest using quantum resonance interferometry; Inventor: Sandeep Gulati; Date of filing: Sep. 2, 2005), the entire contents of which are incorporated herein by reference.

Figure 10:
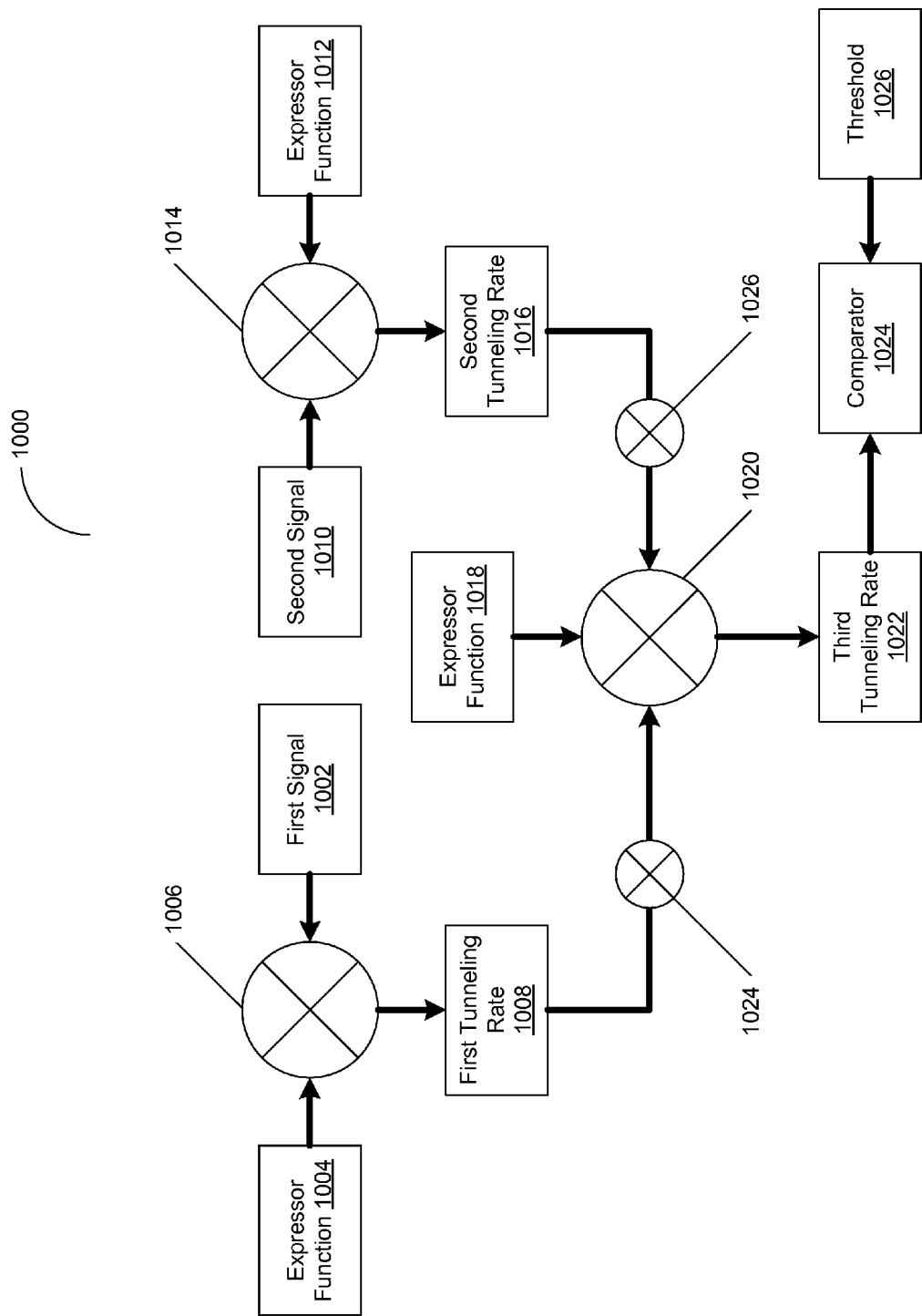
FIG. 10 is a schematic of a system for identifying clutter and signal.

FIG. 10 depicts a schematic of a system 1000 for using QRI to determine if a signal is related to an event of interest or to clutter. In some implementations, the system 1000 can include an expresser function 1004, e.g., a quantum expressor function (QEF). The system 1000 can receive a first signal 1002 and couple the first signal 1002 with the expressor function 1004 using an interferometric coupler 1006, as described previously. The first signal 1002 can be a reference signal. For example, if the object of interest is a human, then a signal from the human can be previously collected and used as the first signal. The output of the interferometric coupling of the expresser function 1004 and the first signal 1002 can be a first tunneling rate 1008 corresponding to the first signal 1002. Similarly, a second signal 1010 can be coupled with an expressor function 1012, e.g., a quantum expressor function, using an interferometric coupler 1014, as discussed previously. The second signal can be the collected signal, wherein the collected signal can include a signal only from the object of interest, a signal from an object that is not the object of interest, or a signal representing a combination of signals from the object of interest and another object. For example, the object of interest can be a human and a reference signal from the human can be previously collected and stored. The unknown signal can represent signal from a human, signal from an undesirable object, e.g., a tree, or a signal from a human standing next to the tree. In this example, the tree represents the clutter which can be identified. The output of the interferometric coupler 1014 can be the second tunneling rate 1016 corresponding to the second signal 1010. The first tunneling rate 1008 corresponding to the first signal 1002 and the second tunneling rate 1016 corresponding to the second signal 1010 can be coupled with an expressor function 1018 using an interferometric coupler 1020. For example, the first tunneling rate 1008 can be interferometrically coupled with the expressor function 1018 and the second tunneling rate 1016 can be interferometrically coupled with the expressor function 1018. In some implementations, the first tunneling rate 1008 and the second tunneling rate 1016 can be pre-conditioned using pre-conditioner 1024 and pre-conditioner 1026, respectively, prior to interferometric coupling using the interferometric coupler 1020. The output from the interferometric coupler 1020 can be the third tunneling rate 1022. The third tunneling rate can be input to a comparator 1024 to which a threshold 1026 can also be input. If the third tunneling rate 1022 is greater than the preset threshold, then the second signal 1010 can match the first signal 1002, i.e., the unknown signal can match the reference signal. If the third tunneling rate 1022 is less than or equal to the preset threshold, the second signal 1010 can be determined to be different from the first signal 1002, i.e., the unknown signal can be different from the reference signal, and can, therefore, be determined to not be a signal of interest.

Figure 11:
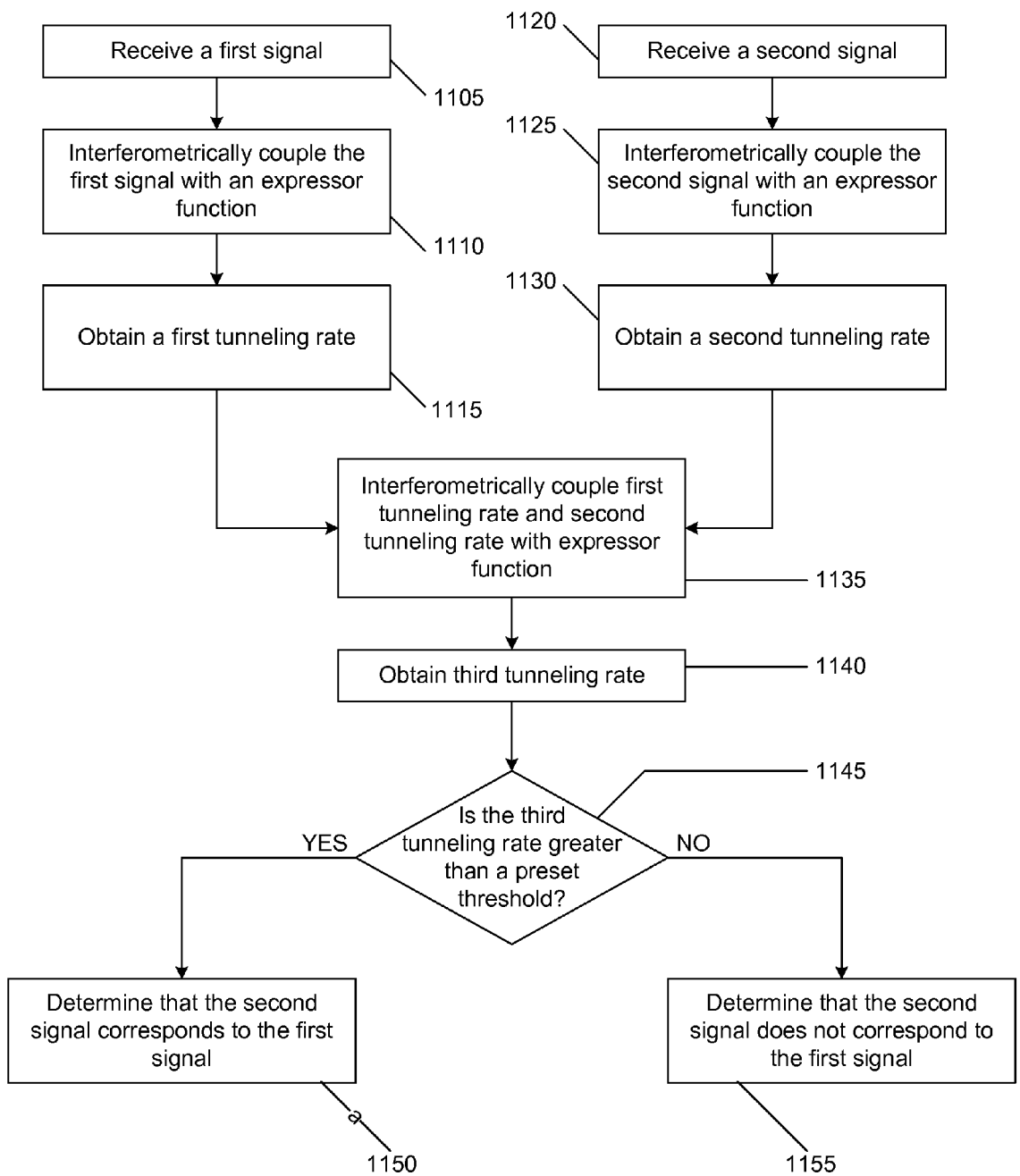
FIG. 11 is a flow chart of an example of a process for identifying clutter and signal.

FIG. 11 is a flow chart of an example of a process for identifying whether a signal is a signal of interest or clutter using QRI. In some implementations, a first signal can be received at 1105. The first signal can be a reference signal and can be obtained from a known source, where the known source is the source of interest. In addition, the first signal can be buried in noise. The first signal can be interferometrically coupled with an expressor function, e.g., a QEF, at 1110, as described previously. The interferometric coupling of the first signal with an expressor function can produce a first tunneling rate which can be obtained at 1115. A second signal can be received at 1120, where the second signal can be obtained from an unknown source. For example, the second signal can relate only to clutter, can relate only to a signal of interest, or can be a combination of a signal of interest and clutter. The second signal can be interferometrically coupled with an expressor function at 1125. The interferometric coupling of the second signal and the expressor function can produce a second tunneling rate that can be obtained at 1130. The first tunneling rate and the second tunneling rate can, each, be coupled with an expresser function at 1135 to obtain a third tunneling rate at 1140. The third tunneling rate can be compared with a preset threshold at 1145. If the third tunneling rate is greater than the preset threshold, then the second signal can be determined to correspond to the first signal. In implementations where the first signal is a reference signal, the second signal can be determined to be a signal of interest at 1150. If the third tunneling rate is less than or equal to the preset threshold, then the second signal can be determined to not correspond to the first signal and can be determined to be clutter at 1155. In some implementations, the first tunneling rate and the second tunneling rate can be pre-conditioned prior to interferometric coupling with an expresser function. Further, the preset threshold can be chosen such that a third tunneling rate greater than the preset threshold indicates clutter while that less than the preset threshold indicates signal.

QRI can operate in a continuous operational mode over a time window of interest, e.g., $\Delta(1, 2, \ldots, \tau)$ clock cycles. At the tunneling rate at an instant "i" can be scalar. Therefore, tunneling rate over time can denote a vector. Therefore, tunneling rate, $TR_A$ is a function of time and tunneling rate can be treated as a data vector. Using Fast Fourier Transform (FFT), $TR_A$ can be transformed into a spectral vector. The tunneling rate spectral vector can be pre-conditioned by methods described in U.S. Pat. No. 7,006,680. The pre-conditioning process can be applied on $TR_{A1}$ to obtain a pre-conditioned input vector corresponding to the first signal, e.g., a reference and well characterized positive signal) and on $TR_{A2}$ to obtain a pre-conditioned input vector corresponding to a second signal, e.g., an unknown signal which may have specific signal or may be only noise or may represent clutter, such as non-specific signal, that can also be denoted as a false positive which looks like signal.

If both the first tunneling rate and the second tunneling rate obtained from the first signal, e.g., reference signal, and the second signal, e.g., unknown signal, respectively, have signal presence, then resonance will be detected upon interferometric coupling. Alternatively, or in addition, the tunneling rate vectors will be indicative of signal presence above background. Subsequently, the two tunneling rates can be processed to determine if the second tunneling rate obtained from the second signal relates to a real signal or a false positive. QRI seeks a resonance between a properly designed QEF and any unknown pre-conditioned input from a dynamical model. Thus, QRI can be used to seek a differential coupling between signal and clutter to identify signal from a false positive. In order to achieve this identification, QRI can be employed for interferometric coupling between a calibrated known signal and unknown signal/clutter input.

In some implementations, the same interferometric coupler used to couple the first signal and the expresser function, and the second signal and the expresser function can be used to couple the first tunneling rate and the second tunneling rate, where the first tunneling rate and the second tunneling rate are pre-conditioned. Thus, the pre-conditioned first tunneling rate, which can represent the tunneling rate from the reference signal, and the pre-conditioned second tunneling rate, which can represent the tunneling rate from the unknown signal, can, each, be interferometrically coupled with an expresser function, e.g., a QEF. The detection of resonance between the pre-conditioned tunneling rates and the QEF can be an indication of the presence of signal. Resonance detection can be based on turning the tunneling rate into an energy scalar and tracking monotonicity of the scalar. The duration of QRI, which can be determined by the number of QRI iterations, can be used to conclude the presence of signal. Thus, the QEF couples with the tunneling rate to conclude the robustness and persistence of signal.

Each QRI iteration can couple the QEF with the incoming signal and simulated quantum-mechanical noise. Thus, the injected quantum-mechanical noise can create spectral harmonics that can be different in signal and clutter. This can be used as the basis for detecting signal as a departure from noise using QRI. In the coupler, the first tunneling rate obtained from the first signal, e.g., the reference signal can be combined with a simulated quantum-mechanical noise and coupled with an expresser function, e.g., QEF. The second tunneling rate obtained from the second signal, e.g., the unknown signal, can be combined with simulated quantum-mechanical noise, and coupled with an expresser function, e.g., QEF. The additive simulated quantum-mechanical system can create a new spectral harmonics in the first tunneling rate, denoted, e.g., by New-TR1, and a new spectral harmonics in the second tunneling rate, denoted, e.g., by New-TR2. These new harmonics in New-TR1 and New-TR2 can cause a change in the coupling between the QEF and New-TR1 that can be denoted, e.g., by $TR_{31}$ and $TR_{32}$, respectively. If $TR_{31}$ and $TR_{32}$ were both resulting from specific signal, then $TR_{31}$ and $TR_{32}$ would have the same properties and statistics, e.g., mean, variance, and the like. The third tunneling rate can be a difference in $TR_{31}$ and $TR_{32}$ and can be a function of time. Further, the third tunneling rate can be converted to a scalar, e.g., by averaging over some integer iteration window. The behavior of the third tunneling rate over time can be used to infer the presence of specific signal or clutter.

In some implementations, the third tunneling rate can be compared against a preset design threshold that can correspond to a condition where the first tunneling rate and the second tunneling rate are both driven by the same reference calibration signal. So, the only difference between the first tunneling rate and the second tunneling rate can be the input quantum-mechanical noise. The expressor function, e.g., QEF, can be designed such that the quantum-mechanical noise can be less than the measurement precision of the system. For example, the third tunneling rate can be concluded to be greater than the threshold if the third tunneling rate is above the baseline, resulting from the first and second tunneling rate interferometric coupling, by at least 3 standard deviations. In this manner, if the third tunneling rate is greater than threshold, it can be concluded that the second signal, e.g., the unknown signal relates to specific signal.

A number of implementations of the invention have been described. Nevertheless, it will be understood that various modifications may be made without departing from the spirit and scope of the invention. For example, the expressor function with which the first signal and the second signal are interferometrically coupled can be the same expressor function or different expressor functions. Similarly, the expressor function with which the first and second tunneling rate are interferometrically coupled can be the same expressor function as that interferometrically coupled with the first signal or the second signal or both. Interferometric coupling of the first signal with an expresser function and the second signal with an expresser function can be performed serially or in parallel. Accordingly, other embodiments are within the scope of the following claims.

What is claimed is:

1. A computer-implemented method for signal analysis comprising:
    receiving a first signal;
    receiving a second signal;
    coupling the first signal with a first function generated from a first quantum mechanical system to generate a first tunneling rate;
    coupling the second signal with a second function generated from a second quantum mechanical system to generate a second tunneling rate;
    coupling the first tunneling rate with a third function generated from a third quantum mechanical system;
    coupling the second tunneling rate with the third function to obtain a third tunneling rate; and
    upon determining that the third tunneling rate is greater than a threshold, identifying that the second signal corresponds to the first signal.

2. The method of claim 1 wherein the first signal is a reference signal and the second signal is an unknown signal.

3. The method of claim 1 wherein the second signal is substantially similar to the first signal if the second signal corresponds to the first signal.

4. The method of claim 1 wherein coupling the first signal with a first function comprises:
    initializing a first dynamical system corresponding to a first modality of the first signal;
    generating a first measurement probe based on the initialized first dynamical system;
    injecting the first measurement probe into the first quantum mechanical system; and
    determining whether the injection of the first measurement probe into the first quantum mechanical system results in a collapse of the first quantum mechanical system.

5. The method of claim 4 wherein a collapse of the first quantum mechanical system indicates resonance between the first measurement probe and the first quantum mechanical system.

6. The method of claim 1 wherein the first tunneling rate and the second tunneling rate are pre-conditioned prior to coupling with the third function.

7. The method of claim 6 wherein pre-conditioning the first tunneling rate and second tunneling rate comprises converting the first tunneling rate and the second tunneling rate into respective spectral domains.

8. A computer-implemented method for signal analysis comprising:
    receiving an unknown signal;
    coupling the unknown signal with a function generated from a quantum mechanical system to generate a tunneling rate associated with the unknown signal;
    pre-conditioning the tunneling rate;
    coupling the pre-conditioned tunneling rate with a reference tunneling rate obtained from a reference signal to generate an output tunneling rate; and
    upon determining that the output tunneling rate is greater than a threshold, determining that the unknown signal corresponds to the reference signal.

9. The method of claim 8 wherein the unknown signal includes one of the reference signal, noise, or a non-specific signal.

10. The method of claim 8 wherein coupling the unknown signal with the function comprises:
    initializing a dynamical system corresponding to a modality of the unknown signal;
    generating a measurement probe based on the initialized dynamical system;
    injecting the measurement probe into the quantum mechanical system; and
    determining whether the injection of the measurement probe into the quantum mechanical system results in a collapse of the quantum mechanical system.

11. The method of claim 10 wherein a collapse of the quantum mechanical system indicates resonance between the measurement probe and the quantum mechanical system.

12. The method of claim 8 further comprising pre-conditioning the tunneling rate by applying a Fast Fourier Transform.

13. The method of claim 8 wherein the reference tunneling rate is pre-conditioned prior to coupling with the pre-conditioned tunneling rate.

14. The method of claim 8 wherein the reference signal is obtained from a known source.

15. The method of claim 8 wherein determining that the unknown signal corresponds to the reference signal comprises determining that the unknown signal is substantially similar to the reference signal.

16. A system for signal analysis comprising:
a function generator to generate a first function, a second function, and a third function from one or more quantum mechanical systems;
a first interferometric coupler to couple a first signal with the first function to generate a first tunneling rate;
a second interferometric coupler to couple a second signal with the second function to generate a second tunneling rate;
a first pre-conditioner to pre-condition the first tunneling rate;
a second pre-conditioner to pre-condition the second tunneling rate;
a third interferometric coupler to couple the pre-conditioned first tunneling rate with the third function and to couple the pre-conditioned second tunneling rate with the third function, the third interferometric coupler configured to generate a third tunneling rate; and
a comparator to compare the third tunneling rate with a threshold to determine if the third tunneling rate is greater than, or less than or equal to the threshold.

17. The system of claim 16 wherein the first signal is a reference signal and the second signal is an unknown signal.

18. The system of claim 16 wherein the second signal is substantially similar to the first signal if the third tunneling rate is greater than the threshold.

19. The system of claim 16 wherein the first interferometric coupler is configured to perform operations comprising:
initializing a first dynamical system corresponding to a first modality of the first signal;
generating a first measurement probe based on the initialized first dynamical system;
injecting the first measurement probe into a first quantum mechanical system; and
determining whether the injection of the first measurement probe into the first quantum mechanical system results in a collapse of the first quantum mechanical system.

20. The system of claim 19 wherein a collapse of the first quantum mechanical system indicates resonance between the first measurement probe and the first quantum mechanical system.

21. A computer-readable medium encoding a computer program product which when executed cause one or more computers to perform operations comprising:
receiving an unknown signal;
coupling the unknown signal with a function generated from a quantum mechanical system to generate a tunneling rate associated with the unknown signal;
pre-conditioning the tunneling rate;
coupling the pre-conditioned tunneling rate with a reference tunneling rate obtained from a reference signal to generate an output tunneling rate; and
upon determining that the output tunneling rate is greater than a threshold, determining that the unknown signal corresponds to the reference signal.

22. The computer-readable medium of claim 21 wherein the unknown signal includes one of the reference signal, noise, or a non-specific signal.

23. The computer-readable medium of claim 21 wherein coupling the unknown signal with the function comprises:
initializing a dynamical system corresponding to a modality of the unknown signal;
generating a measurement probe based on the initialized dynamical system;
injecting the measurement probe into the quantum mechanical system; and
determining whether the injection of the measurement probe into the quantum mechanical system results in a collapse of the quantum mechanical system.

24. The computer-readable medium of claim 23 wherein a collapse of the quantum mechanical system indicates resonance between the measurement probe and the quantum mechanical system.

25. The computer-readable medium of claim 21 the operations further comprising pre-conditioning the tunneling rate by applying a Fast Fourier Transform.

26. The computer-readable medium of claim 21 wherein the reference tunneling rate is pre-conditioned prior to coupling with the pre-conditioned tunneling rate.

27. The computer-readable medium of claim 21 wherein the reference signal is obtained from a known source.

28. The computer-readable medium of claim 21 wherein determining that the unknown signal corresponds to the reference signal comprises determining that the unknown signal is substantially similar to the reference signal.

* * * * *